US012742006B2

(12) United States Patent
Clemmensen et al.

(10) Patent No.: US 12,742,006 B2
(45) Date of Patent: Sep. 22, 2026

(54) GLP1R AGONIST NMDAR ANTAGONIST CONJUGATES

(71) Applicant: KØBENHAVNS UNIVERSITET, Copenhagen K (DK)

(72) Inventors: Christoffer Clemmensen, Copenhagen K (DK); Anders Bue Klein, Copenhagen K (DK); Jonas Odgaard Petersen, Copenhagen K (DK); Bente Flensborg Frølund, Copenhagen K (DK); Kristian Strømgaard, Copenhagen K (DK)

(73) Assignee: KØBENHAVNS UNIVERSITET, Copenhagen K (DK)

( * ) Notice: Subject to any disclaimer, the term of this patent is extended or adjusted under 35 U.S.C. 154(b) by 892 days.

(21) Appl. No.: 17/925,818

(22) PCT Filed: Jun. 3, 2021

(86) PCT No.: PCT/EP2021/064930

§ 371 (c)(1),
(2) Date: Nov. 16, 2022

(87) PCT Pub. No.: WO2021/245199

PCT Pub. Date: Dec. 9, 2021

(65) Prior Publication Data

US 2023/0183335 A1 Jun. 15, 2023

(30) Foreign Application Priority Data

Jun. 3, 2020 (EP) .................................... 20178057

(51) Int. Cl.

| | |
|---|---|
| ***A61K 47/55*** | (2017.01) |
| ***A61K 47/64*** | (2017.01) |
| ***A61P 1/16*** | (2006.01) |
| ***A61P 3/04*** | (2006.01) |
| ***A61P 3/10*** | (2006.01) |
| ***C07K 16/26*** | (2006.01) |
| ***C07K 16/28*** | (2006.01) |

(52) U.S. Cl.

CPC ................ *C07K 16/26* (2013.01); *A61P 3/04* (2018.01); *C07K 16/286* (2013.01)

(58) Field of Classification Search

CPC ......... C07K 16/26; C07K 16/286; A61P 3/04; A61P 1/16; A61P 3/06; A61P 3/10; A61K 47/64; A61K 47/55; A61K 38/26

See application file for complete search history.

(56) References Cited

U.S. PATENT DOCUMENTS

| | | | |
|---|---|---|---|
| 8,536,122 | B2 | 9/2013 | Lau et al. |
| 2019/0300571 | A1 | 10/2019 | Cudic et al. |

FOREIGN PATENT DOCUMENTS

| | | | |
|---|---|---|---|
| JP | 2009517420 | A | 4/2009 |
| JP | 2014527986 | A | 10/2014 |
| WO | WO 2007/046834 | A2 | 4/2007 |
| WO | WO 2007/076319 | A2 | 7/2007 |
| WO | WO 2008/080042 | A2 | 7/2008 |
| WO | WO 2011/143208 | A1 | 11/2011 |
| WO | WO 2011/163012 | A2 | 12/2011 |
| WO | WO 2019/092618 | A2 | 5/2019 |

OTHER PUBLICATIONS

Collins et al, "NMDA Receptor Antagonists for the Treatment of Neuropathic Pain," Pain Medicine 11:1726-1742 (2010) (Year: 2010).*

Drumm et al, Genetic Variation and Clinical Heterogeneity in Cystic Fibrosis, Annu. Rev. Pathol. Mech. Dis., 2012, 7, pp. 267-282 (Year: 2012).*

Yampolsky et al, The Exchangeability of Amino Acids in Proteins, Genetics, 2005, 170, pp. 1459-1472 (Year: 2005).*

Quarta et al., "Molecular Integration of Incretin and Glucocorticoid Action Reverses Immunometabolic Dysfunction and Obesity", Cell Metabolism, Oct. 2017, 26: 620-632.

Rammes, "Neramexane: a moderate-affinity NMDA receptor channel blocker: new prospects and indications", Expert Rev. Clin. Pharmacol., 2009, 2(3): 231-238.

Bech et al., "Peptide Half-Life Extension: Divalent, Small-Molecule Albumin Interactions Direct the Systemic Properties of Glucagon-Like Peptide 1 (GLP-1) Analogues", Journal of Medicinal Chemistry, 2017, 60: 7434-7446.

Brennan et al., "Memantine in the Treatment of Binge Eating Disorder: An Open-Label, Prospective Trial", Int J Eat Disord, 2008; 41(6): 520-526.

Deng et al., "Long-Term NMDAR Antagonism Correlates Weight Loss With Less Eating", Frontiers in Psychiatry, 2019), 10:15, 7 pages.

Hermanussen et al., "A new anti-obesity drug treatment: first clinical evidence that, antagonising glutamate-gated Ca2+ ion channels with memantine normalises binge-eating disorders", Economics & Human Biology, 2005, 3: 329-337.

Lee et al., "Thyroid Hormone Regulation of N-Methyl-D-Aspartic Acid Receptor Subunit mRNA Expression in Adult Brain", Journal of Neuroendocrinology, 2003, 15: 87-92.

(Continued)

*Primary Examiner* — Julie Ha
*Assistant Examiner* — Kristina M Hellman
(74) *Attorney, Agent, or Firm* — James S. Keddie; Bozicevic Field & Francis LLP

(57) ABSTRACT

A conjugated molecule comprising a peptide displaying at least 0.1% activity of native glucagon-like peptide 1 (GLP-1) at the GLP-1 receptor, and an N-methyl-D-aspartate receptor (NMDAR) antagonist is provided. The peptide is covalently bonded to the NMDAR antagonist either directly or through a chemical linker. The conjugated molecule has use in therapy. A pharmaceutical composition comprising the conjugated molecule, a method of reducing body weight of a mammal comprising administering the conjugated molecule to the mammal, and a non-therapeutic method of reducing body weight of a mammal comprising orally administering the conjugated molecule to the mammal are also provided.

14 Claims, 18 Drawing Sheets

Specification includes a Sequence Listing.

(56) References Cited

OTHER PUBLICATIONS

Marquard et al., "Characterization of pancreatic NMDA receptors as possible drug targets for diabetes treatment", Nature Medicine, 2015, 21(4): 363-372.
Parlevliet et al., "CNTO736, a Novel Glucagon-Like Peptide-1 Receptor Agonist, Ameliorates Insulin Resistance and Inhibits Very Low-Density Lipoprotein Production in High-Fat-Fed Mice", The Journal of Pharmacology and Experimental Therapeutics, 2009, 328(1): 240-248.
Petersen et al., "Designing Poly-agonists for Treatment of Metabolic Diseases: Challenges and Opportunities", Drugs, 2019, 79: 1187-1197.
Popik et al., "Memantine reduces consumption of highly palatable food in a rat model of binge eating", Amino Acids, 2011, 40: 477-485.
Sherwood et al., "The Origin and Function of the Pituitary Adenylate Cyclase-Activating Polypeptide (PACAP)/Glucagon Superfamily*", Endocrine Reviews, 2000, 21(6): 619-670.
Smith et al., "The Uncompetitive N-methyl-D-Aspartate Antagonist Memantine Reduces Binge-Like Eating, Food-Seeking Behavior, and Compulsive Eating: Role of the Nucleus Accumbens Shell", Neuropsychopharmacology, 2015, 40: 1163-1171.
Soleymani-Goloujeh et al., "Effects of N-terminal and C-terminal modification on cytotoxicity and cellular uptake of amphiphilic cell penetrating peptides", Artificial Cells, Nanomedicine, and Biotechnology, 2018, 46(S1): S91-S103.
Dods et al., "The peptide agonist-binding site of the glucagon-like peptide-1 (GLP-1) receptor based on site-directed mutagenesis and knowledge-based modelling", Bioscience Reports, 2016, 36(1):e00285.
Gupta, "Glucagon-like peptide-1 analogues: An overview", Indian Journal of Endocrinology and Metabolism, 2013, 17(3): 413-421.
Jazayeri et al., "Crystal structure of the GLP-1 receptor bound to a peptide agonist", Nature, Jun. 2017, 546: 254-258.
Longwell et al., "Identification of N-Terminally Diversified GLP-1R Agonists Using Saturation Mutagenesis and Chemical Design", ACS Publications, Dec. 2020, 16: 58-66.
Song et al., "Human GLP-1 receptor transmembrane domain structure in complex with allosteric modulators", Nature, Jun. 2017, 546: 312-315.
Yaginuma et al., "High-throughput identification of peptide agonists against GPCRs by co-culture of mammalian reporter cells and peptide-secreting yeast cells using droplet microfluidics", Scientific Reports, Jul. 2019, 9:10920.

* cited by examiner

GLP-1 Pen40 + → GLP-1 Pen40

GLP-1 Cys40
SH
+
N
S-S
O
O
N

GLP-1 Cys40
S-S
O
O
N

Fig. 18

GLP-1 hCys40
SH
+
N
S-S
O
O
N

GLP-1 hCys40
S-S
O
O
N

Fig. 19

GLP-1 Pen40 SH

GLP-1 Pen40

Vehicle
GLP-1Pen40
GLP-1Pen40/MK801
GLP-1Lys40-triazole-PEG4-Val-Cit-PAB-MK801
GLP-1Cys40-Maleimido-mc-Val-Cit-PAB-MK801

Vehicle
GLP-1Pen40
GLP-1Pen40/MK801
GLP-1Lys40-triazole-PEG4-Val-Cit-PAB-MK801
GLP-1Cys40-Maleimido-mc-Val-Vit-PAB-MK801

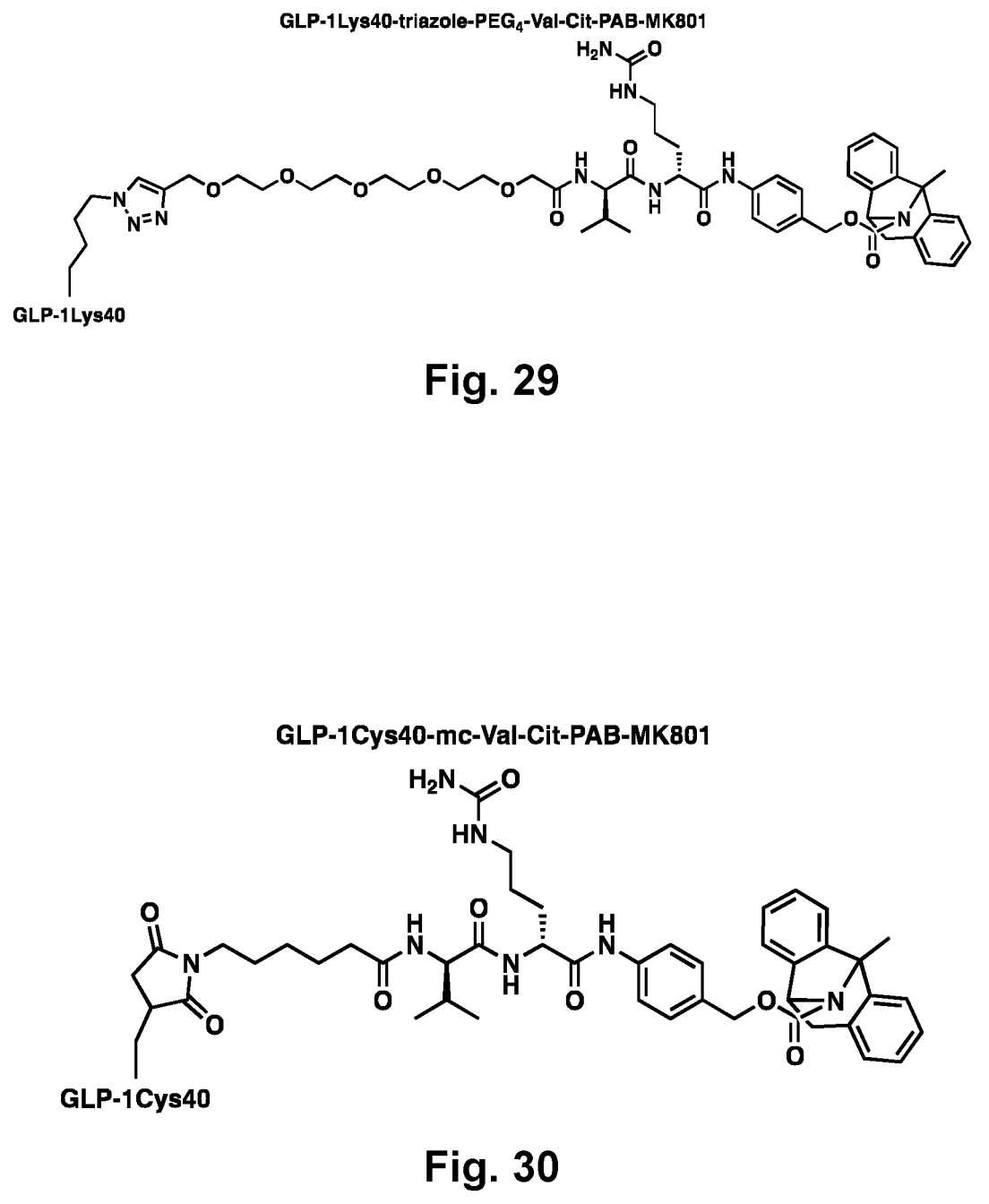

GLP-1Lys40-triazole-PEG$_4$-Val-Cit-PAB-MK801

H$_2$N O HN O N H O N H N H O O N N=N O O O O GLP-1Lys40 N O O

Fig. 29

GLP-1Cys40-mc-Val-Cit-PAB-MK801

H$_2$N O HN O N O O N H O N H N H O O GLP-1Cys40 N O O

Fig. 30

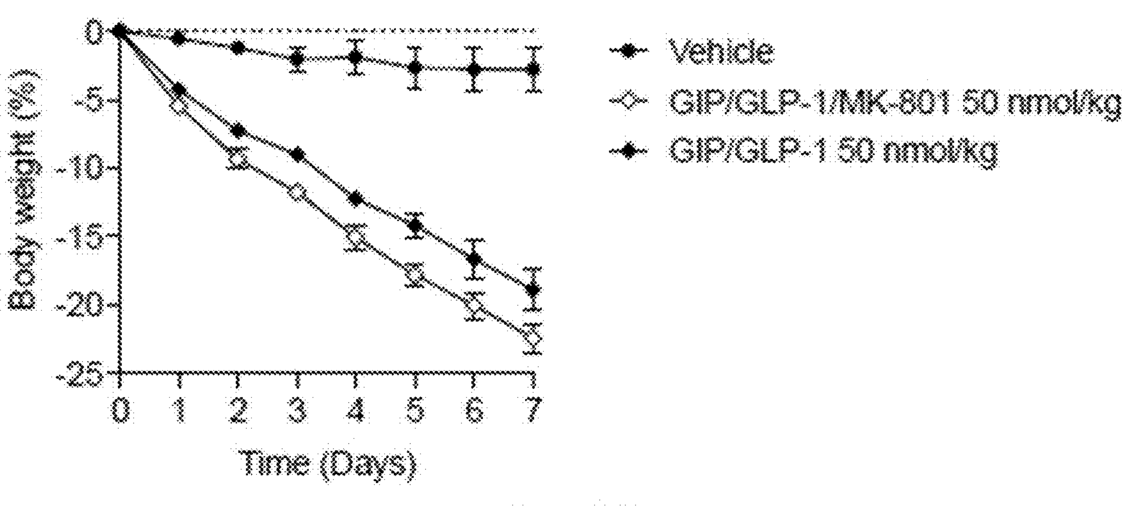
Fig. 33
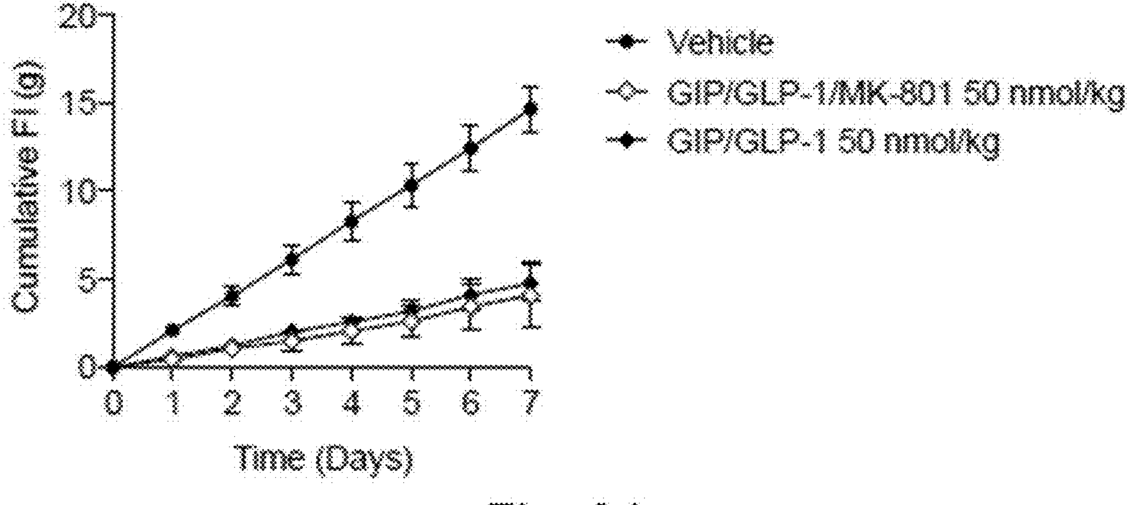
Fig. 34
GLP-1/GIPPen40/MK801 YX$_1$EGT FTSDY SIYLD KQAAX$_3$EFVNW LLAGG PSSGA PPPSX$_2$
GLP-1Pen40/MK801 HX$_1$EGT FTSDV SSYLE EQAAK EFIAW LVKGG PSSGA PPPSX$_2$
8 differential amino acids: 80% homology
Without the $C_{ex}$ tail: 71% homology
Fig. 35

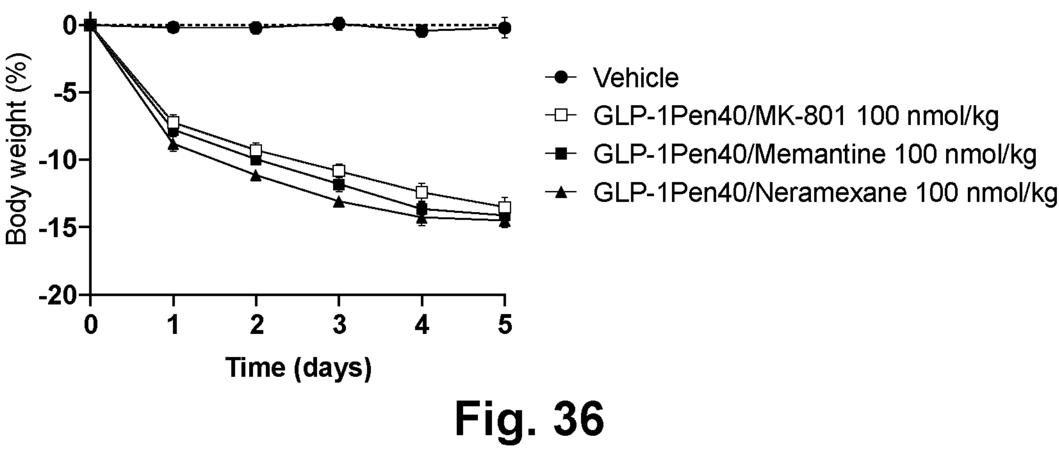
Fig. 36
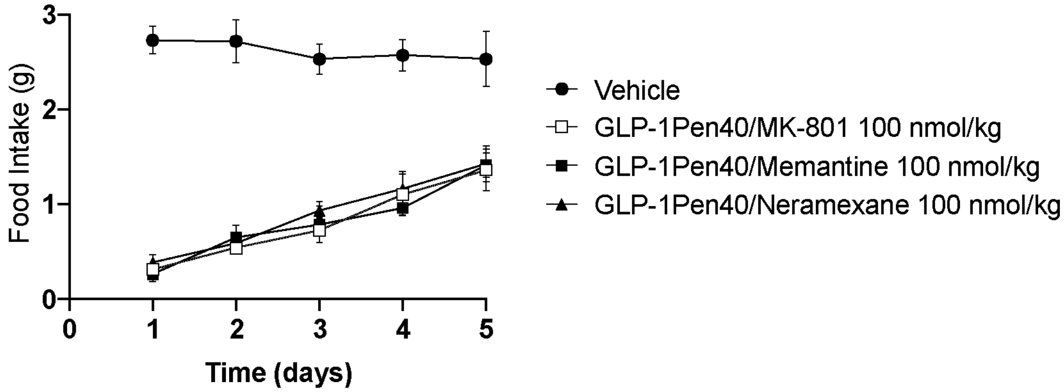
Fig. 37
Cumulative FI (g)
15
10
5
0
0 1 2 3 4 5
Time (days)
Vehicle
GLP-1Pen40/MK-801 100 nmol/kg
GLP-1Pen40/Memantine 100 nmol/kg
GLP-1Pen40/Neramexane 100 nmol/kg
Fig. 38

GLP1R AGONIST NMDAR ANTAGONIST CONJUGATES

CROSS-REFERENCE TO RELATED APPLICATIONS

This application is a § 371 national phase of International Application No. PCT/EP2021/064930, filed on Jun. 3, 2021, which claims the benefit of European Application No. 20178057.4, filed on Jun. 3, 2020, which applications are incorporated by reference herein.

TECHNICAL FIELD

The present invention relates generally to the field of therapeutic conjugates and more specifically to conjugates having glucagon-like peptide 1 (GLP-1) receptor activity and an N-methyl-D-aspartate receptor (NMDAR) antagonist.

BACKGROUND ART

Obesity is the most prevalent nutritional disease of humans and domestic animals such as dogs and cats in affluent societies, exceeding by far the number of nutritional deficiency diseases. As alternatives to bariatric surgery, many attempts have been made to generate weight-lowering drugs for the treatment of obesity. This has resulted in drugs that act by preventing the absorption of fats by acting as lipase inhibitors in the gut, or by inhibiting food intake via selective serotonin receptor 2C agonism in the hypothalamus.

Glucagon-like peptide 1 (GLP-1) is a 30 or 31 amino acid long peptide hormone derived from the tissue-specific post-translational processing of the proglucagon peptide. A recent indication of GLP-1 analogues is for weight loss, since it acts on the appetite regulating centres of the brain. GLP-1 is of relevance to appetite and weight maintenance because it has actions on the gastrointestinal tract as well as effects on the CNS involved in the regulation of appetite. It also delays gastric emptying and gut motility in humans, which could contribute to regulating food intake. GLP-1-based therapies for treatment of metabolic diseases are known from the prior art. Parlevliet et al. (J Pharmacol Exp Ther. 2009 January; 328(1):240-8)" and related patent applications EP1968645 A2, EP2125003 A2, and EP1843788 A2 describe the use of a human GLP-1 Mimetibody™ comprising a GLP-1 peptide for treating obesity and obesity-related disorders. More specifically, Parlevliet et al. (2009) describe a specific GLP-1 CNTO 736, which can decrease food intake and body weight, due to the reduction in fat mass, in high-fat-fed mice.

NMDAR antagonists act by inhibiting the action of the NMDA receptor and there is some pre-clinical evidence that supports NMDAR antagonism might be relevant for appetite reduction and weight maintenance. Deng et al. (2019, Frontiers in Psychiatry, 10, Article 15) describe the use of memantine hydrochloride, an NMDAR antagonist, driving a weight loss in diet-induced obese mice induced by high fat diet. Smith et al. (Neuropsychopharmacology (2015) 40, 1163-1171) describe that memantine can dose-dependently decreased binge-like eating and fully block food-seeking behavior and compulsive eating, selectively in rats subjected to a highly palatable, high-sugar diet. Also, Popik et al. (Amino Acids (2011) 40:477-485) describe that chronically administered memantine hydrochloride in rats can selectively decrease consumption of highly palatable food with less effect on the consumption of a standard diet, and that this effect persists after the treatment is discontinued.

The effect of memantine in treatment of binge-eating disorder in humans has also been reported. Hermanussen and Tresguerres (Economics and Human Biology 3 (2005) 329-337), report a therapeutic trial with five obese young women that memantine treatment may lead to markedly decreased appetite and suppressed binge-eating disorder within the first 24 hours and lead to a decrease in body weight within a few days. Brennan et al. (Int J Eat Disord 2008; 41:520-526) describe a preliminary study showing that memantine administered daily for 12 weeks may improve binge-eating in human subjects.

There is a growing need for novel weight loss treatments with greater efficacy, high safety (low toxicological effect), which also offers convenient and safe administration options.

SUMMARY OF THE INVENTION

In view of the above, it is therefore an object of the present invention to provide an effective and safe therapeutic agent to reduce food intake and lower body weight in obese human subjects.

Accordingly, a first aspect of the present invention relates to a conjugated molecule comprising a peptide displaying at least 0.1% activity of native GLP-1 at the GLP-1 receptor and an N-methyl-D-aspartate receptor (NMDAR) antagonist, the peptide being covalently bonded to the NMDAR antagonist either directly or through a chemical linker.

The inventors have surprisingly found that conjugation of peptides with GLP-1 receptor agonism and NMDAR antagonism represents a novel medicinal strategy for effectively reversing obesity. Conjugates based on this strategy are superior in suppressing food intake relative to the GLP-1 peptide, memantine or MK801 alone, as shown in FIGS. 3 to 13. Also, it has been shown that conjugates based on GLP-1 peptide variants, e.g. GLP-1/Gastric inhibitory polypeptide (GIP) peptide (SEQ ID NO:9), and alternative NMDAR antagonists have similar beneficial effects on food intake and body weight reduction. This is supported by the further findings testing the GLP-1/GIP co-agonist and the NMDAR antagonist neramexane, as shown in FIGS. 33 to 34 and FIGS. 36 to 38, respectively. Further, while the conjugates benefit from the effects of NMDAR antagonism on weight loss, central nervous system effects of NMDAR antagonism are circumvented by this strategy. Without being bound by any particular theory, the inventors speculate that this effect is achieved by the NMDAR antagonist accumulating at and/or close to the sites of GLP-1 receptors in the body due to the affinity of the peptide towards GLP-1 receptors.

A peptide will have an amino terminus and a carboxyl terminus. In the context of the invention, the amino terminus and the carboxyl terminus may also be referred to as the N-terminus and the C-terminus, respectively, and corresponding derived forms.

The peptide may consist of amino acids encoded by the genetic code or it may contain amino acids encoded by the genetic code and natural amino acids, which are not encoded by the genetic code, such as hydroxyproline, γ-carboxyglutamate, ornithine, phosphoserine, D-alanine (dAla), and D-glutamine. Further, the peptide may incorporate synthetic amino acids such as D-alanine, and D-leucine, or a-aminoisobutyric acid (Aib), d-Serine (dSer), N-methyl-serine.

In a preferred embodiment, the amino acid on position 2 (counted from the N-terminal) in the peptide is dSer, dAla, Aib, glycine, N-Methyl-Ser or valine.

The peptide may also have one or more modifications to stabilise secondary structure, such as cyclisation between a glutamic acid on position 15 and a lysine on position 20 of the peptide, the positions being counted from the N-terminal.

The peptide may be obtained from any source or the peptide may be produced as desired. For example, the peptide may be isolated from a tissue, or the peptide may be produced recombinantly or synthesized by methods that are well known to the person skilled in the art.

The conjugated molecule comprises a peptide, the peptide (in its free form) displaying at least 0.1% activity of native GLP-1 at the GLP-1 receptor. In the context of the present invention, GLP-1 receptor activity, which may also be referred to as GLP-1 activation (GLP-1R activity), can be measured in an in vitro assay by measuring cAMP induction in HEK293 cells over-expressing the GLP-1 receptor. Specifically, HEK293 cells co-transfected with DNA encoding the GLP-1 receptor and a luciferase gene linked to cAMP responsive element (reporter assay) may be used. The assay may be carried out as described by Bech et al. (*J. Med. Chem.* 2017, 60, 17, 7434-7446). Using this assay, the GLP-1 R activity from each of the conjugates can be determined and presented relative to the activity obtained by native GLP-1 (SEQ ID NO:1) peptide in the same assay. In an embodiment, the peptide of the conjugate displays at least 1% activity of native GLP-1, such as at least 5%, 10%, 15%, 20%, or 30% activity.

The NMDAR antagonist will bind to the NMDAR, and the NMDAR antagonist may be described as having a dissociation constant $K_d$ with a specified NMDA receptor, e.g. in the free form of the NMDAR antagonist. NMDAR antagonists generally have dissociation constants in the nanomolar range, for instance the dissociation constant of MK801 with NMDA receptors of different species are $K_d$=6.3 nM in brain membranes of rats, $K_d$=10 nM in brain homogenates of mice, and $K_d$ 1.3 nM in pig brains. Determination of dissociation constants is well-known to the skilled person. In one embodiment, the NMDAR antagonist in its free form has a dissociation constant $K_d$ with an NMDA receptor in the range of 0.5 nM to 1000 nM, e.g. in the range of 0.5 nM to 100 nM.

The NMDA receptor may for example be a human NMDA receptor, e.g. the NMDAR antagonist has a $K_d$ with human NMDA receptor in the range of 0.5 nM to 100 nM. In the context of the present invention, the NMDA receptor antagonist in its free form refers to the antagonist not being bound, especially chemically linked, to any chemical group and thus being in its native, unmodified form. A person skilled in the art will appreciate that only minor species variation between NMDA receptors is to be expected. It follows that a $K_d$ value measured for rodents, such as mice or rats, or measured for higher mammals, such a pigs, would be expected to be similar to a $K_d$ value measured for human NDMA receptors or other relevant animal or mammalian NMDA receptors.

The peptide of the conjugated molecule may be any peptide having at least 0.1% activity of native GLP-1 at the GLP-1 receptor. In an embodiment, the peptide of the conjugate is of the glucagon-superfamily. The glucagon-superfamily is a group of peptides related in structure in their N-terminal and C-terminal regions (see, for example, Sherwood et al., Endocrine Reviews 21: 619-670 (2000), which is incorporated herein by reference). Members of this group include all glucagon related peptides, as well as Growth Hormone Releasing Hormone (SEQ ID NO:2), vasoactive intestinal peptide (SEQ ID NO:3), pituitary adenylate cyclase-activating polypeptide 27 (SEQ ID NO:4), Secretin (SEQ ID NO:5), Gastric inhibitory polypeptide (GIP) (SEQ ID NO:6), Exendin-4 (SEQ ID NO:7), GLP-1 unmodified (SEQ ID NO:8), GLP-1/GIP co-agonist (SEQ ID NO:9) and analogues, derivatives or conjugates with up to 1, 2, 3, 4, 5, 6, 7, 8, 9 or 10 amino acid modifications relative to the native peptide. Such peptides preferably retain the ability to interact (as an agonist) with receptors of the glucagon receptor superfamily, preferably the GLP-1 receptor. The peptide of the conjugated molecule may have at least 80% amino acid sequence identity to SEQ ID NO:2, SEQ ID NO:3, SEQ ID NO:4, or SEQ ID NO:5. Also, the peptide of the conjugated molecule may have at least 80% amino acid sequence identity to SEQ ID NO:6, SEQ ID NO:7, SEQ ID NO:8, or SEQ ID NO:9. In specific embodiments, the peptide of the conjugated molecule has the amino acid sequence of SEQ ID NO:2, SEQ ID NO:3, SEQ ID NO:4, or SEQ ID NO:5. In other specific embodiments, the peptide of the conjugated molecule has the amino acid sequence of SEQ ID NO:6, SEQ ID NO:7, SEQ ID NO:8, or SEQ ID NO:9. In an embodiment the peptide of the invention is exenatide, liraglutide, lixisenatide, albiglutide, dulaglutide, or semaglutide.

Also contemplated are peptides with co-agonist activity which display the ability to bind to different receptors of the glucagon receptor superfamily. In one embodiment such co-agonist is a GLP-1/GIP receptor co-agonist. The effect of conjugated molecules based on a co-agonist of SEQ ID NO:9 and NMDAR antagonist on food intake and body weight is shown in FIGS. 33 to 34.

In an embodiment, the peptide of the conjugate has at least 80% amino acid sequence identity to SEQ ID NO:1. For example, the peptide may have at least about 80%, at least about 85%, at least about 90%, at least about 95%, or more than about 97% identity to SEQ ID NO:1. In a specific embodiment, the peptide has the amino acid sequence of SEQ ID NO:1. Such a peptide may have a significantly greater GLP-1 activity at the GLP-1 receptor compared to native GLP-1 at the GLP-1 receptor. As such, the peptide may, if conjugated to an NMDAR antagonist, accumulate at a greater rate at the site of GLP-1 receptors, which in turn may lead to a greater efficacy of the NMDAR antagonist. An example of a peptide of the conjugate having at least 80% amino acid sequence identity to SEQ ID NO: 1 is shown in FIG. 35, the effect of this peptide being supported by FIGS. 33 to 34. The alignment between GLP-1/GIP Pen40/MK801 (peptide according to SEQ ID NO:9) and GLP-1 Pen40/MK801 (peptide according to SEQ ID NO:1) is further illustrated below:

GLP-1/GIPPen40/MK801
$YX_1EGT$ FTSDY SIYLD $KQAAX_1$ EFVNW LLAGG PSSGA $PPPSX_2$

GLP-1Pen40/MK801
$HX_1EGT$ FTSDV SSYLE EQAAK EFIAW LVKGG PSSGA $PPPSX_2$

The peptide of the conjugated molecule will have a length sufficient for the peptide (in its free form), to display at least 0.1% activity of native GLP-1 at the GLP-1 receptor. In general, this can be observed for peptides comprising at least 10 amino acids, but the activity may not be displayed when the peptide comprises more than 60 amino acids. Thus, in an embodiment, the peptide has a length in the range of 10 to 60 amino acids, e.g. 20 to 50 amino acids. Amino acid sequences of the present invention that are identical to other peptides sequences to a certain percentage should comprise enough of the amino acid sequence of a peptide, e.g. at least 10 amino acids, to afford putative identification of that peptide, either by manual evaluation of the sequence by one skilled in the art, or by computer-automated sequence comparison and identification using algorithms such as BLAST (Basic Local Alignment Search Tool) (for a review see Altschul, et al., Meth Enzymol. 266: 460, 1996; and Altschul, et al., Nature Genet. 6: 119, 1994).

In the context of the present invention, peptide may differ in %-identity by having substitutions, insertions of natural or synthetic amino acids and/or having amino acid deletions. In one embodiment, wherein the peptide of the conjugate has the amino acid sequence of SEQ ID NO:1.

In an embodiment, the peptide is modified by acetylation, fatty acid conjugation, diacid conjugation, albumin conjugation, small-molecule albumin binders, and/or PEG conjugation. Also contemplated are peptides modified by linking to carrier proteins, such as antibodies. The modifications are preferably at position 16, 17, 20, 21, 24, 29, 40 of the peptide (counted from the N-terminal), within a C-terminal region, or at the C-terminal amino acid. The conjugation may be made by any suitable linker, such as by disulfide, maleimide, alpha-ketone, or click-chemistry based conjugation. The skilled person knows how to prepare such conjugates. Preferably, PEG molecules may be larger than 1 kDa and fatty acids and diacids may contain more than 12 carbon atoms. It is generally preferred to add a spacer between the modification (PEG/fatty acid/diacid) and the peptide, the linker preferably being a gamma-Glu linker, a short PEG chain.

The conjugated molecule comprises an NMDAR antagonist. Any NMDAR antagonist may be used with the conjugate. However, it is preferred that the NMDAR antagonist is a small molecule, e.g up to 900 kDa. For example, in one embodiment, the NMDAR antagonist is selected from MK801, memantine, ketamine, phencyclidine (PCP), neramexane and amantadine. MK801, neramexane and memantine are preferred. Also preferred are MK801 and memantine. Neramexane is a non-limiting example of a compound related to memantine, and the effect of neramexane is shown in FIGS. 36 to 38.

The peptide of the invention and the NMDAR antagonist are covalently bonded. In the context of the present invention, the conjugated molecule may also be referred to as a peptide-drug-conjugate (PDC). The peptide and the NMDAR antagonist may be bonded directly to each other. For example, the NMDAR antagonist may be bonded covalently through an amide bond, the amide bond being from the amino group on a NMDAR antagonist to a carboxylic acid group on the peptide. Such an amide bond may be made to any residue on the peptide having a carboxylic acid group such as a glutamic acid residue, an aspartic acid residue, a synthetic residue with a carboxylic acid group, or the carboxylic acid of the C-terminal. For example, when the NMDAR antagonist is MK801, the amine of MK801 may be bound to a carboxylic acid of an amino acid residue of the peptide. Correspondingly, when the NMDAR antagonist is memantine, the amine of memantine may be bound to a carboxylic acid of an amino acid residue of the peptide.

In the context of the present invention, being directly covalently bonded means that the peptide has a covalent bond with the NMDAR antagonist, e.g. there are no additional chemical groups between the two molecules, such as a linker group. The peptide and the NMDAR antagonist may also be bonded through a chemical linker. Any chemical linker may be used. However, it is generally preferred that the chemical linker has a length of up to 30 atoms. A longer chain may have the advantage of distancing the NMDAR antagonist from the peptide, such that the NMDAR antagonist is of no or little steric hindrance to the peptide, when the peptide interacts with a GLP-1 receptor. No or low steric hindrance of the peptide affords a greater affinity towards the GLP-1 receptor. A conjugate with a greater affinity towards the GLP-1 receptor is likely to have a greater accumulation at the site of GLP-1 receptors. The chemical linkers are preferably cleavable linkers, such as acid-cleavable linkers, enzyme-cleavable linkers, peptide-cleavable linkers, or disulfide linkers, which are generally well-known in the art for their use in peptide-drug conjugates. Examples of such cleavable linkers are compounds comprising glucuronide, beta-galactoside, disulfide, hydrazone and/or which compounds are cleavable by galactosidases, glucuronidases, pyrophospatases, phosphatases, arylsulfatases, proteases, or esterases. For instance, a linker may comprise a peptide cleavable by cathepsin, such as GFLG. The linker may further comprise a 4-aminobenzoic acid (PAB), that may be covalently bonded to the amino group of the NMDAR antagonist through an amide or carbamate bond. The linkers preferably release the NMDAR antagonist in its free form (i.e. native form), which may be achieved by many different linker chemistries such as the disulfide linkers disclosed herein. These linker chemistries and additional linker chemistries are well-known by the skilled person.

In one embodiment, the NMDAR antagonist is covalently bonded at the C-terminal region of the peptide. In the context of the invention, the C-terminal region may be up to 50% of the amino acids counted from the C-terminus, such as up to 40%, 30%, 25%, 20%, or 10% of the amino acids counted from the C-terminus. For instance, the C-terminal region of SEQ ID NO:1 may be amino acids 21 to 40, 26 to 40, or 31 to 40 (numbers counted from N-terminal). Thus, the NMDAR antagonist, e.g. memantine or MK801, may be bonded, either directly or via a linker, to any one of the 10 amino acids counted from the C-terminus. For example, the NMDAR antagonist, e.g. memantine or MK801, may be bonded directly to an amino acid within 5 amino acids from the C-terminus. Thereby the NMDAR antagonist produces little or no steric hindrance at the N-terminal of the peptide. As the N-terminal is involved in binding to the GLP-1 receptor, no or low steric hindrance of the N-terminal may afford a greater affinity towards the GLP-1 receptor. A conjugate with a greater affinity towards the GLP-1 receptor is likely to have a greater accumulation at the site of GLP-1 receptors. It is also contemplated that more than one NMDAR antagonist may be bonded to the same peptide molecule.

In another highly preferred embodiment, the NMDAR antagonist is covalently bonded to the peptide via a chemical linker comprising a disulfide group. A disulfide group allows that the NMDAR antagonist is released from the peptide when chemically reduced. A chemical linker comprising a disulfide group, also known as a disulfide linker, ensures that the peptide and the NMDAR antagonist of the conjugate remain conjugated for an extended period during systemic circulation. The disulfide group of the disulfide linker may be reduced in a reducing environment, such as an intracellular environment, resulting in the conjugate being cleaved such that the peptide part of the conjugate is separated from the NMDAR antagonist part of the conjugate. The reduction may be through disulfide exchange with e.g. a thiol, such as glutathione or reductases such as intracellular protein disulfide-isomerase enzymes. The chemical linker may be chosen from chemical linkers known in the art with the general formula R'—S—S—R", in which the R' and R" groups may be identical or different from each other. Experiments have shown that conjugates of a peptide and an NMDAR antagonist, which are conjugated through a chemical linker comprising a disulfide group, have a human plasma cleavage half-time of about 0.5 to 13 hours, as seen in FIG. 3. Advantageously, the conjugate may accumulate at and/or close to the sites of GLP-1 receptors in the body due to the affinity of the peptide towards GLP-1 receptors, and the NMDAR antagonist may be released at the sites and/or close to the sites of the GLP-1 receptors. When free from peptide part of the conjugate, the NMDAR antagonist may have a suitably effect as site-specific NMDAR binding. It is speculated by the inventors that the conjugate may be cleaved in the extracellular environment immediately adjacent to cells harbouring GLP-1 receptors, or that the conjugate may be internalized by the cells harbouring GLP-1 receptors and cleaved in the reducing environment of the cells.

In one embodiment, the conjugated molecule is conjugated via a chemical linker, wherein the chemical linker has the formula $R_1$-$R_3$—S—S—$R_4$-$R_5$—O—CO—$R_2$, wherein $R_1$ is the peptide, $R_2$ the NMDAR antagonist, $R_3$ is optional and when present is selected from $C(CH_3)_2$, $CH_2$—$CH_2$, or $CH_2$, bonded to a side chain of the peptide or to a carbon atom of the backbone chain of the peptide, $R_4$ is $(CH_2)_n$ or $C_6H_4$, $R_5$ is optional and when present is selected from $C(CH_3)_2$, $CH_2$—$CH_2$, or $CH_2$, and n is 1, 2, or 3. When the chemical linker is reduced, the liberated NMDAR antagonist part of the conjugate undergoes intramolecular cyclisation which leads to the release of the NMDAR antagonist into its free form, see FIG. 1B.

In one embodiment, the chemical linker has the formula $R_1$-$R_3$—S—S—$(CH_2)_n$—O—CO—$R_2$, wherein $R_1$ is the peptide, $R_2$ the NMDAR antagonist, $R_3$ is optional and when present is selected from $C(CH_3)_2$, $CH_2$—$CH_2$, or $CH_2$, bonded to a side chain of the peptide or to a carbon atom of the backbone chain of the peptide, and n is 1, 2, or 3.

In one embodiment, the chemical linker has the formula $R_1$-$R_4$-$R_3$—S—S—$(CH_2)_n$—O—CO—$R_2$, wherein $R_1$ is the peptide, $R_2$ the NMDAR antagonist, $R_3$ is optional and when present is selected from $CH(CH_3)_2$, $CH_2$—$CH_2$, or $CH_2$, bonded to a side chain of the peptide or to a carbon atom of the backbone chain of the peptide, $R_4$ is optional and when present is selected from $CH(CH_3)_2$, $CH_2$—$CH_2$, or $CH_2$, bonded to a side chain of the peptide or to a carbon atom of the backbone chain of the peptide and n is 1, 2, or 3.

In an embodiment, the second radical bond is to the backbone of the peptide of the invention.

In another embodiment, the second radical bond is to a side chain of the peptide of the invention.

In the context of the present invention, when $R_1$ is bonded to the backbone chain of the peptide, $C(CH_3)_2$ (L-penicillamine) may be referred to as Pen, $CH_2$—$CH_2$ (L-homocysteine) may be referred to as hCys, and $CH_2$ (L-Cysteine) may be referred to as Cys, see FIG. 1A.

As used herein, the first and the second radical bond is used to state the presence of at least two free bonds in the chemical linkers disclosed herein.

The present invention facilitates the design and synthesis of a library of conjugated molecules comprising a peptide and an NMDAR antagonist appended via chemical linkers. FIG. 1 shows how such conjugated molecules, may be designed. As shown in FIG. 1A, the conjugate may be prepared by chemically bonding an NMDAR antagonist (MK801 in FIG. 1) to a peptide. The skilled person will appreciate that a vast number of different chemical linkers may be prepared by the methods disclosed herein and by other methods reported in literature, and these chemical linkers may be used to append peptides and NMDAR antagonists according to the methods disclosed herein and as reported elsewhere in the known art.

The inventors have surprisingly found that the peptide of the present invention may serve a bifunctional role as a weight lowering drug and a targeting agent, allowing for site-selective delivery of otherwise non-specific small-molecules, such as NMDAR antagonists, to regions of the brain governing feeding, which could be, but is not limited to, hypothalamic nuclei, area postrema, the nucleus of the solitary tract and the ventral tegmental area. Thus, the conjugated molecule of the present invention provides an avenue to selectively modulate glutamatergic signalling in brain regions governing food intake, while circumventing it from freely signalling throughout the entire brain. It is understood, that the targeting properties of the peptide of the present invention may also facilitate delivery of the NMDAR antagonists to other sites, such as for example the endocrine pancreas.

The conjugated molecule disclosed herein provides selectivity and also up-concentrates drug action in the targeted region. This targeting enabled by the conjugated molecule allows for an improved therapeutic index, i.e. a lower minimum effective concentration. Furthermore, the coupling allows to add-on another layer of metabolic drug action to the efficacy of GLP-1 receptor targeting medicines. Tissue-selective targeting of NMDARs may be used for management of feeding behaviour and may attenuate relapse after treatment cessation as a result of reconsolidated synaptic plasticity at a lower body weight set-point.

The inventors have demonstrated a surprising synergistic effect of the conjugates of the invention on appetite, food intake, and body weight, and this is significantly greater in comparison to the effect obtained with the administration of peptide or the drug alone, see FIGS. 4 to 14. The surprising synergistic effect of the conjugates of the invention are further supported by the findings shown in FIGS. 21 to 28 and FIGS. 33 to 34 and FIGS. 36 to 38.

The inventors have further demonstrated a surprising synergistic effect of the conjugates of the invention on food reward and satiety, and this is significantly greater in comparison to the effect obtained with the administration of the peptide or the drug alone, see FIG. 31.

Additionally, the synergistic effect of the conjugates of the invention has been demonstrated to be relevant in treatment of diabetic patients, see FIG. 32.

Thus, the administration of the conjugates of the present invention results in an unexpected reduction in food intake, and body weight in obese animals.

In an embodiment of the present invention the conjugated molecule is for use in therapy.

In an embodiment, the conjugated molecule of the present invention is for use in the treatment of obesity, binge-eating disorder, insulin resistance, type 2 diabetes, dyslipidaemia, non-alcoholic steatohepatitis, or non-alcoholic fatty liver disease.

Another aspect of the present invention relates to a pharmaceutical composition comprising the conjugated molecule according to the invention, and a pharmaceutically acceptable carrier. Any embodiment of the conjugated molecule may be used in the pharmaceutical composition.

In a further aspect, the invention relates to the use of the conjugated molecule according to the invention in the manufacture of a pharmaceutical composition. In particular, the pharmaceutical composition is for use in the treatment of obesity, binge-eating disorder, insulin resistance, type 2 diabetes, dyslipidaemia, non-alcoholic steatohepatitis, or non-alcoholic fatty liver disease. Any embodiment of the conjugated molecule may be used in the manufacture of the pharmaceutical composition.

The data disclosed in the present invention have been obtained in studies of mice, but the conclusions are equally relevant for humans, since the major hormonal pathways governing energy metabolism are similar between mice and humans at they display comparable receptor expression profiles.

The conjugate of the present invention may be administered in the form of a pharmaceutical composition. Accordingly, the present invention further provides a pharmaceutical composition, which comprises a conjugate of the present invention or a pharmaceutically acceptable salt thereof, and a pharmaceutically acceptable carrier. The pharmaceutical formulations may be prepared by conventional techniques. Briefly, pharmaceutically acceptable carriers can be either solid or liquid. Solid form preparations include powders, tablets, pills, capsules, cachets, suppositories, and dispersible granules. A solid carrier can be one or more excipients which may also act as diluents, solubilisers, lubricants, suspending agents, binders, preservatives, wetting agents, tablet disintegrating agents or an encapsulating material.

The conjugate comprised in the pharmaceutical formulation may be in powder form, obtained by aseptic isolation of sterile solid or by lyophilisation from solution for constitution before use with a suitable vehicle, e.g., sterile, pyrogen-free water.

In one embodiment, the pharmaceutical composition is suited for subcutaneous administration, intramuscular administration, intraperitoneal administration, intravenous administration or for oral administration. Accordingly, the compositions of the present invention may be provided in unit dose form in ampoules, pre-filled syringes, small volume infusion or in multi-dose containers, optionally with an added preservatives. The compositions may take such forms as suspensions, solutions or emulsions in oily or aqueous vehicles.

In accordance with the current disclosure, pharmaceutical compositions are provided wherein the and food intake lowering effects of peptides with GLP-1R activity are combined with NMDAR antagonism in a single modality. Active delivery via peptides with GLP-1R activity to the hypothalamic nuclei, area postrema, the nucleus of the solitary tract and the ventral tegmental area and/or the endocrine pancreas segregates archetypical NMDAR-mediated unwanted neurobiological effects, such as for examples dissociative, psychotic, behavioural effects, from positive metabolic effects. Unwanted neurobiological effects caused by NMDAR antagonism may include hallucinations, paranoid delusions, confusion, difficulty concentrating, agitation, alterations in mood, nightmares, catatonia, ataxia, anaesthesia, and learning and memory deficits. Positive metabolic effects of NMDAR antagonists may include improvements in glucose metabolism, decreased food intake and suppression of binge-eating disorder, which may be beneficial for reducing obesity and obesity-related metabolic disorders in humans or mammal.

Thus, the therapeutic utility of a peptide of the invention and NMDAR antagonist pairing offers a new approach for the treatment of obesity and its associated metabolic disorders. Treatment of obesity may be achieved by reducing food intake and food motivation and through lowering binge-eating episodes by administration of the conjugated molecule to a human or mammal, and thus, a further aspect of the present invention relates to a method of reducing body weight in a mammal comprising administering the conjugated molecule of the invention or the pharmaceutical composition of the invention.

In an embodiment, the method of lowering body weight entails reducing food intake of the mammal by administering the conjugated molecule of the invention or the pharmaceutical composition of the invention to the mammal.

The conjugated molecule or the pharmaceutical composition may be administered subcutaneously, orally, intramuscularly, intraperitoneally, or intravenously.

The conjugated molecule, and thus also the pharmaceutical composition, is superior in suppressing food intake compared to the prior art. Therefore, the conjugated molecule and the pharmaceutical composition may be used in the treatment of obesity at any level. Obesity may be described in terms of the body mass index (BMI), which is defined as the body mass divided by the square of the body height, e.g. as expressed in units of $kg/m^2$. Without being bound by theory, the present inventors consider that the BMI can be used to define a limit between pathogenic obesity and non-pathogenic obesity. For example, in the context of the invention, a BMI of 30 $kg/m^2$ may be interpreted as the limit between pathogenic obesity and non-pathogenic obesity. However, other values of BMI can also be considered to define the limit between pathogenic obesity and non-pathogenic obesity. Thus, for example, BMI values of 24 $kg/m^2$, 26 $kg/m^2$, 27 $kg/m^2$, 28 $kg/m^2$, 29 $kg/m^2$, 30 $kg/m^2$, 31 $kg/m^2$, 32 $kg/m^2$, 33 $kg/m^2$, 34 $kg/m^2$, and 35 $kg/m^2$ are considered to define the limit between pathogenic obesity and non-pathogenic obesity. In a further aspect, the present invention relates to a non-therapeutic treatment of mammals for reducing body weight, which comprises orally administering to said mammal the conjugated molecule according to the invention. For example, the mammal may have a non-pathogenic BMI. In particular, the method may comprise orally administering the conjugated molecule to a subject having a BMI below the limit defining non-pathogenic obesity.

In the above, the invention has mainly been described with reference to a few embodiments. However, as is readily appreciated by a person skilled in the art, other embodiments than the ones disclosed above are equally possible within the scope of the invention.

Other aspects and advantageous features of the present invention are described in detail and illustrated by non-limiting working examples below.

Generally, all terms used herein are to be interpreted according to their ordinary meaning in the technical field, and applicable to all aspects and embodiments of the invention, unless explicitly defined or stated otherwise. All references to "a/an/the [conjugate, molecule, linker, peptide, etc.]" are to be interpreted openly as referring to at least one instance of said conjugate, agent, molecule, linker, peptide, etc., unless explicitly stated otherwise.

In the context of the present invention, the term "GLP1", "GLP-1" or "GLP1 peptide" means a peptide of the glucagon-superfamily, in particular the incretin hormone glucagon-like peptide 1. The Peptide of the invention may also be considered to be food intake regulating hormone peptides and to function as an active delivery agent of the conjugated molecule of the present invention to the hypothalamus and/or pancreas.

In the context of the present invention, the term “peptide” means a compound composed of stretch of 10 to 60 amino acids connected by peptide bonds.

In the context of the present invention, a peptide derived from GLP-1 is meant as a peptide having amino acid sequence identity to the native GLP-1 peptide, i.e. SEQ ID NO:1, it originates from.

The term “derivative” as used herein in relation to a peptide or an amino acid means a chemically modified peptide or amino acid, wherein at least one substituent is not present in the unmodified peptide or amino acid or analogues thereof, i.e. a peptide or an amino acid which has been covalently modified. Typical modifications are amides, carbohydrates, alkyl groups, acyl groups, esters and the like.

In the context of the present invention, the term “percentage identity” or “% identity” means % of identical amino acids between two compared peptides, in particular using the BLAST algorithm.

The term “NMDAR antagonist” as used herein means a compound which is an antagonist of the NMDA receptor (NMDAR). Examples of NMDAR antagonist include, but are not limited to, memantine, memantine hydrochloride, amantadine, ketamine or MK801. Further examples of NMDAR antagonist include, but are not limited to, norketamin and neramexane.

BRIEF DESCRIPTION OF FIGURES

The above, as well as additional objects, features, and advantages of the present invention is better understood through the following illustrative and non-limiting detailed description of embodiments of the present invention, with reference to the appended drawings, wherein:

FIG. 16 shows an example synthesis route for the conjugation of peptides and small molecules with amino groups.

FIG. 17 shows a synthetic route for synthesizing a chemical linker derivatized MK801.

FIG. 18 shows a conjugation reaction of a linker derivatized MK801 with a peptide (the peptide having an amino acid sequence given by SEQ ID NO:1).

FIG. 19 shows the synthetic route for chemical synthesis of a linker derivatized MK801.

FIG. 20 shows a reaction for conjugation of linker derivatized MK801 with a peptide having the amino acid sequence of SEQ ID NO:1 and having the Pen40 modification.

FIG. 29 is the GLP-1/MK801 conjugate with one type of linker.

FIG. 30 is the GLP-1/MK801 conjugate with one type of linker.

FIG. 33 shows the effect of the co-agonist GIP/GLP-1/MK801 conjugate on body weight in mice.

FIG. 34 shows the effect of the co-agonist GIP/GLP-1/MK801 conjugate on cumulative food intake in mice.

FIG. 35 shows an amino acid sequence alignment between co-agonist GLP-1/GIP of SEQ ID NO: 9 and the GLP-1 peptide of SEQ ID NO: 1 used in the drug conjugates, wherein $X_1$ is D-alanine, D-serine, alpha-aminoisobutyric acid, N-methyl-serine, glycine, or valine, and $X_2$ is cysteine (hCys40/Cys40) or L-penicillamine (Pen40).

FIG. 36 shows the effect of different NDMAR antagonists conjugated with GLP-1 Pen40 on body weight in mice.

FIG. 37 shows the effect of different NDMAR antagonists conjugated with GLP-1 Pen40 on daily food intake in mice FIG. 38 shows the effect of different NDMAR antagonists conjugated with GLP-1 Pen40 on cumulative food intake in mice.

DETAILED DESCRIPTION

Figure 1:
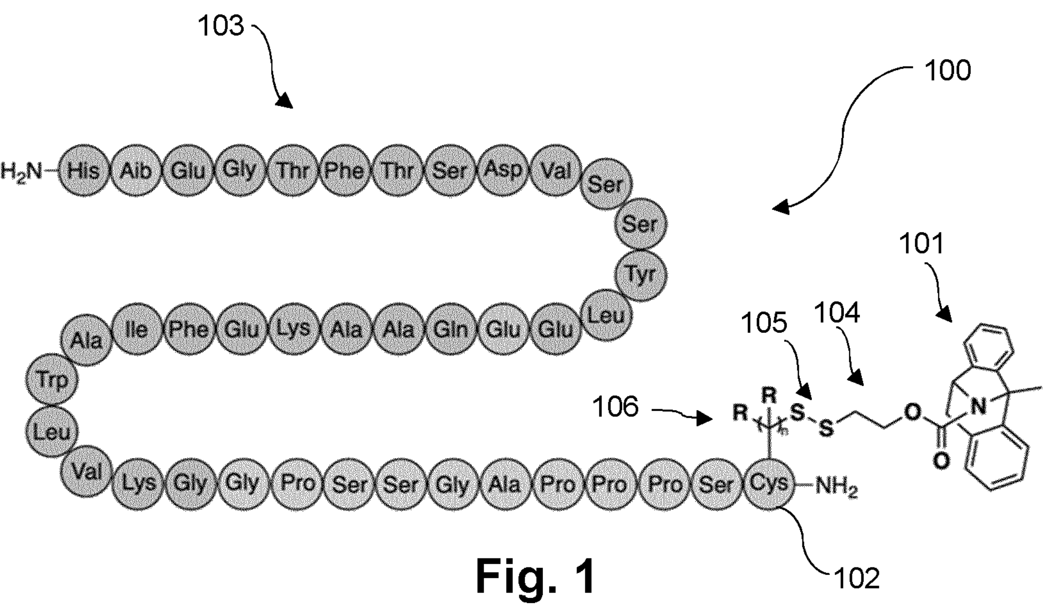
FIG. 1 shows an example of a peptide and NMDAR antagonist conjugate.

FIG. 1 shows an example of a peptide and NMDAR antagonist conjugate 100, which consists of MK801 101 chemically appended to a C-terminal cysteine 102 of the peptide of SEQ ID NO:1 103 through a chemical linker 104, the chemical linker 104 comprising a disulfide group 105. A side chain 106 of the C-terminal cysteine 102, may optionally be derivatised, such that length n of the side chain 106 is 1 or 2 carbon atoms and/or R is hydrogen or methyl. A modification called hCys40 of the side chain 106 has length n=2 carbon atom and R=hydrogen. A modification called hCys40 of the side chain 106 has length n=1 carbon atom and R=methyl. Regular cysteine is called Cys40.

Figure 2:
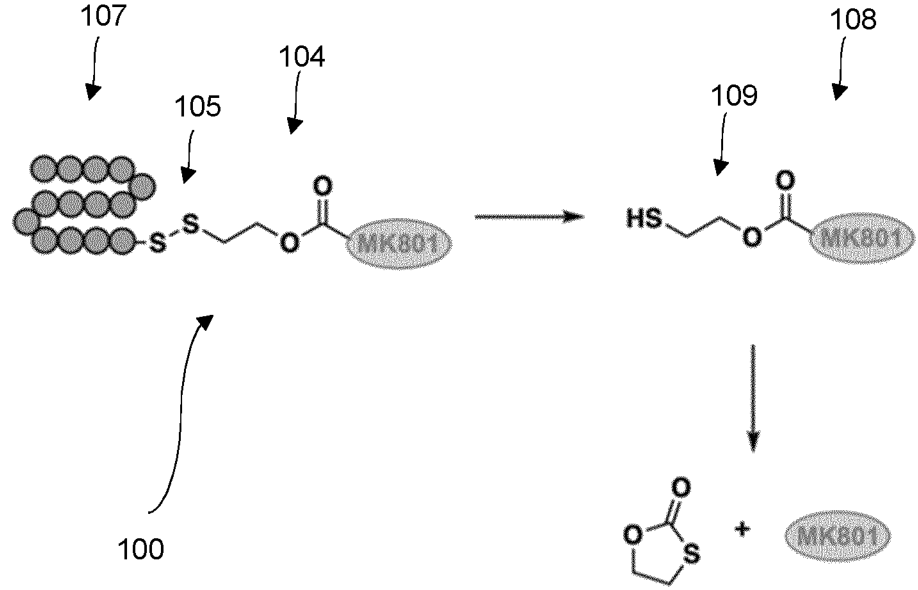
FIG. 2 displays the mechanism by which MK801 is released from the conjugate of FIG. 1.

FIG. 2 displays the mechanism by which MK801 is released from the conjugate 100 of FIG. 1. The chemical linker 104 comprising a disulfide group 105 is self-immolative and may be reduced in a reducing environment (not shown) such as an intracellular environment to produce thiol groups, separating the peptide part of the conjugate 107 from the MK801 part 108 of the conjugate. On the MK801 part 108 of the molecule, a liberated nucleophilic thiol 109 undergoes spontaneous intramolecular cyclization to release MK801 as the native unmodified MK801 drug (free form of MK801).

Figure 3:
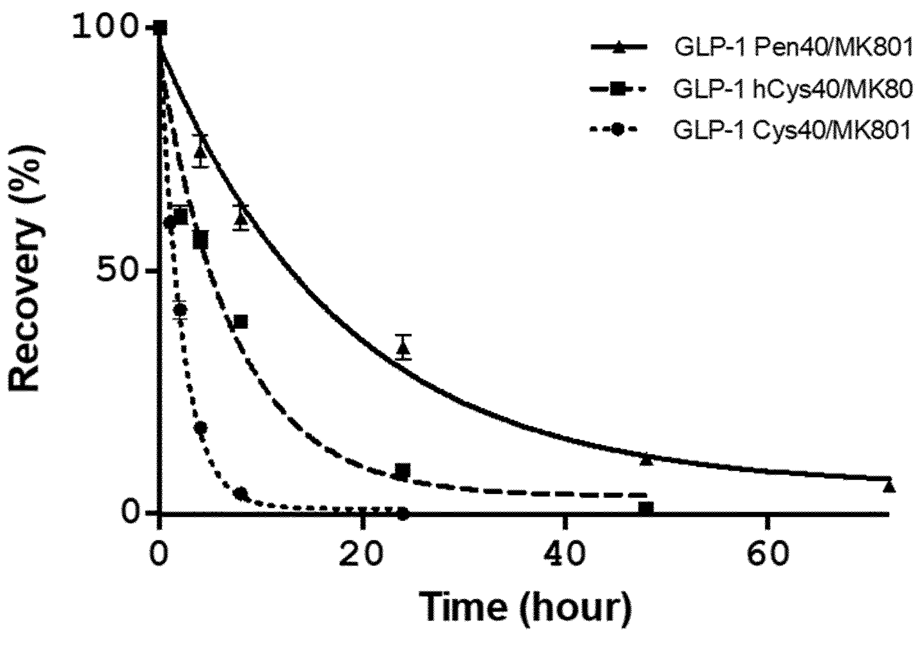
FIG. 3 shows the in vitro human plasma stability of three versions of the conjugate of FIGS. 1 and 2.

FIG. 3 shows the in vitro human plasma stability of three versions of the conjugate 100 of FIGS. 1 and 2, each version having a different cysteine derivative or residue. The first version GLP-1 Pen40/MK801 has cysteine derivative Pen40, the second version GLP-1 hCys40/MK801 has the cysteine derivate hCys40, and the third version GLP-1 Cys40/MK801 has an unmodified cysteine Cys40. The plasma stability of each version is shown as percentage recovery over time. LCMS analysis (not shown) revealed that the major contribution to conjugate degradation originates from deconjugation of MK801 likely by disulfide exchange of the linker. Consequently, single substitution of the C-terminal cysteine 102 (hCys40/Cys40) to L-penicillamine (Pen40) drastically increased the plasma stability by decreasing the accessibility of the disulfide bond due to increased steric hindrance.

FIG. 4-14 display the results of the in vivo mice studies disclosed in example 8.

Figure 4:
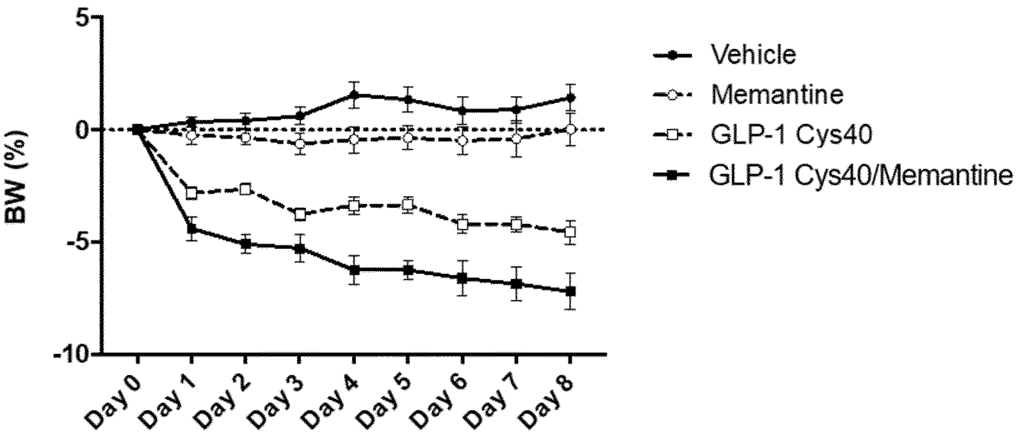
FIG. 4 shows the weight-lowering effect of a conjugate of a peptide of SEQ ID NO:1 and memantine (GLP-1 Cys40/Memantine)

FIG. 4 shows the weight-lowering effect of a conjugate of a peptide of SEQ ID NO:1 and memantine chemically appended via the linker shown in FIGS. 1 and 2, wherein the cysteine residue is unmodified cysteine (GLP-1-Cys40/Memantine) (40 nmol/kg) and equimolar doses of the peptide of SEQ ID NO:1 (GLP-1 Cys40) or memantine measured in body weight percentage (BW %) of diet induced (DIO) mice treated for 8 days. Data is expressed as mean±SEM and N is 8 per group. Both GLP-1 Cys40 and GLP-1 Cys40/Memantine resulted in a lowered BW % in the DIO mice, the latter conjugate resulting in approximately 7% BW % reduction after 8 days of treatment.

Figure 5:
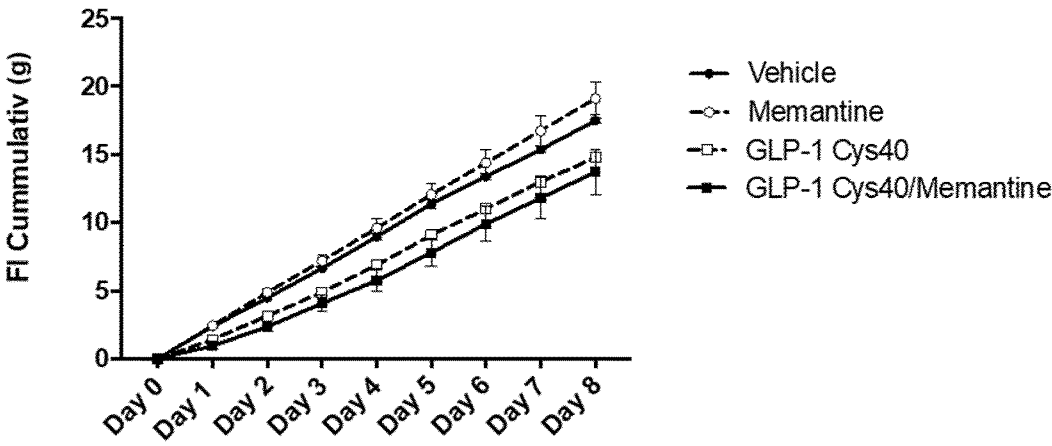
FIG. 5 shows the effect of GLP-1 Cys40/Memantine on cumulative food intake in mice.

FIG. 5 shows the effect of GLP-1 Cys40/Memantine and equimolar doses of GLP-1 Cys40 or memantine on cumulative food intake (FI Cumulative, gram per day) in DIO mice treated for 8 days. Data is expressed as mean±SEM and N=8 per group. Over the course of the treatment, a lowered cumulative food intake was observed in mice treated with GLP-1 Cys40 and GLP-1 Cys40/Memantine compared to the control (vehicle) and to memantine.

Figure 6:
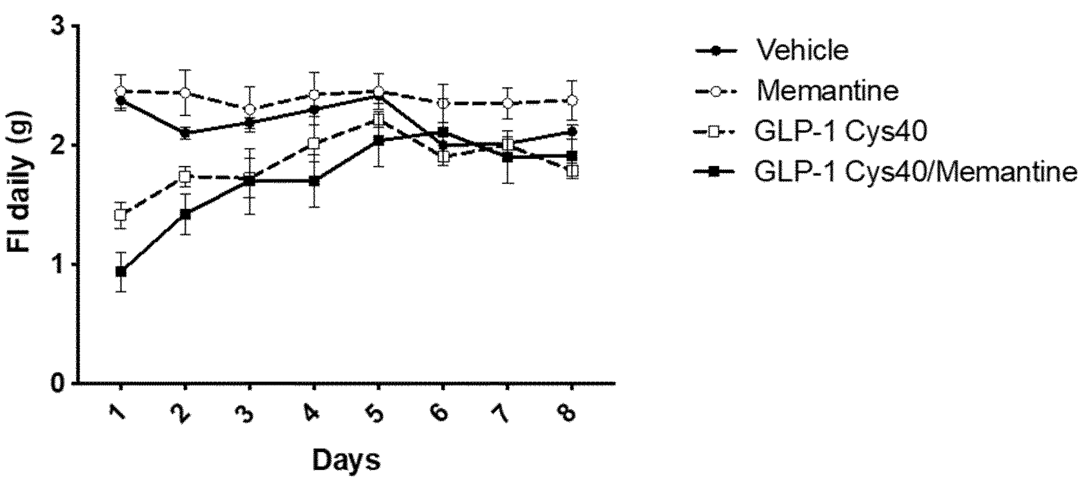
FIG. 6 shows the effect of GLP-1 Cys40/Memantine on daily food intake in mice.

FIG. 6 shows the effect of GLP-1 Cys40/Memantine (40 nmol/kg) or equimolar doses of GLP-1 Cys40 or memantine on daily food intake (FI daily, gram per day) in DIO mice treated for 8 days. Data is expressed as mean±SEM and N=8 per group. During the 8 days of treatment, GLP-1 Cys40 and GLP Cys40/Memantine showed in general a lowered daily food intake compared to the memantine-treated mice and the control group (vehicle, i.e. saline). At the end of the study, mice treated with GLP-1 showed only a slight reduction in food intake compared to the control group (vehicle).

Figure 7:
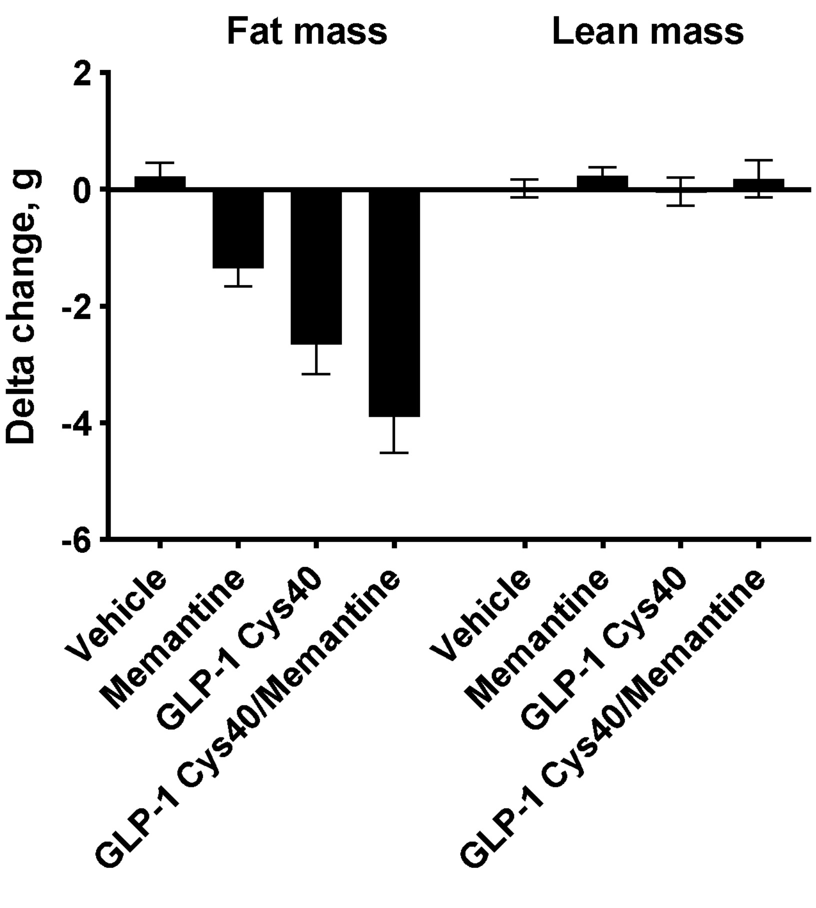
FIG. 7 shows the effect of GLP-1 Cys40/Memantine on body composition in mice.

FIG. 7 shows the effect of GLP-1 Cys40/Memantine (40 nmol/kg) or equimolar doses of GLP-1 Cys40 or memantine on body composition (Delta change, g), in terms of change in fat and lean body mass, in DIO mice treated for 8 days. Data is expressed as mean±SEM and N=8 per group. After 8 days, mice treated with memantine, GLP-1 Cys40, and GLP-1 Cys40/Memantine all displayed a reduction in fat body mass, while nearly no change was seen in lean body mass. GLP-1 Cys40/Memantine resulted in the highest change in fat body mass with approximately 4 g fat mass reduction observed in the mice treated with this conjugate.

Figure 8:
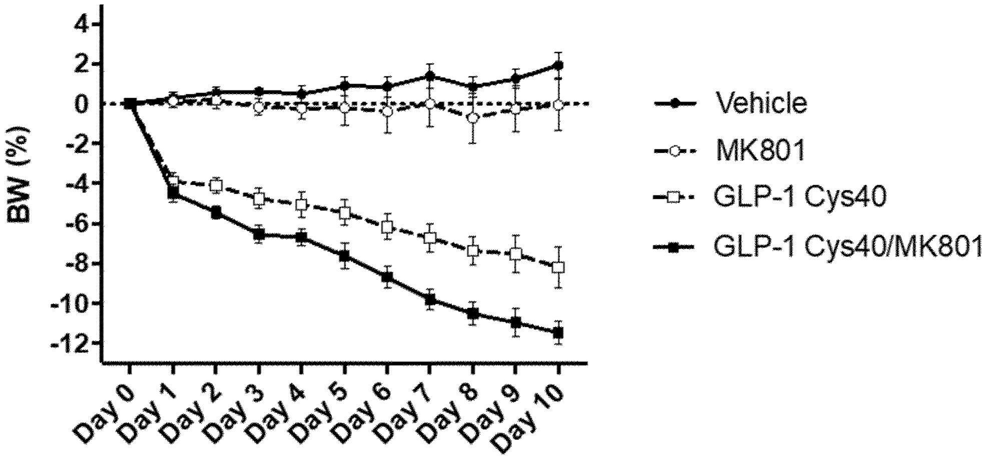
FIG. 8 shows the weight-lowering effect of a conjugate of a peptide of SEQ ID NO:1 and MK801 (GLP-1 Cys40/MK801)

FIG. 8 shows the weight-lowering effect (BW %) of GLP-1 Cys40/MK801 (100 nmol/kg) or equimolar doses of GLP-1 Cys40 or MK801 in DIO mice treated for 10 days. Data is expressed as mean±SEM and N=8 per group. While MK801 showed nearly no percentage change in body weight (BW), both GLP-1 Cys40 and GLP-1 Cys40/MK801 resulted in approximately 8 and 12% reduction in BW, respectfully, after 10 days of treatment.

Figure 9:
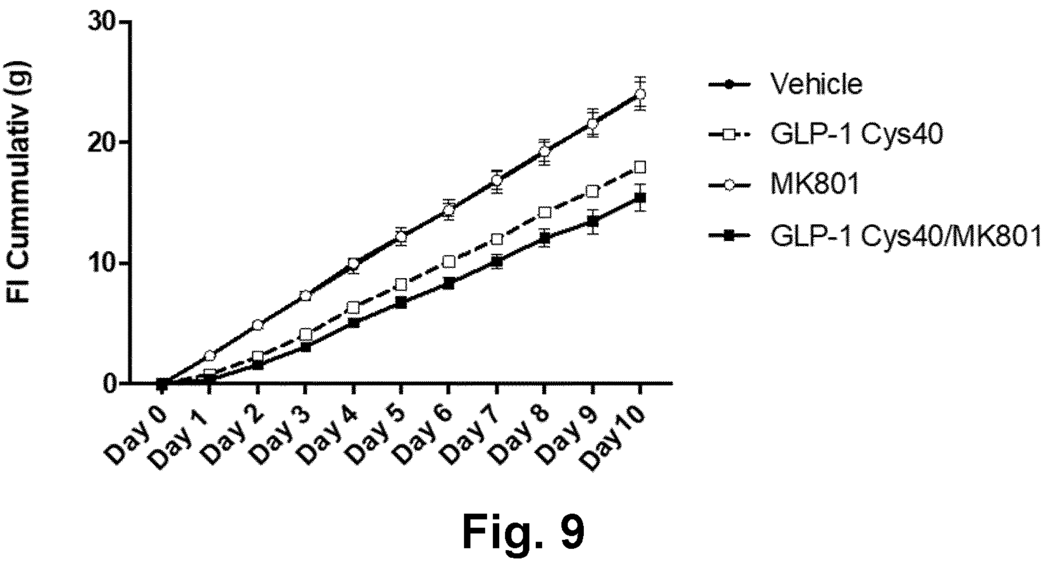
FIG. 9 shows the effect of GLP-1 Cys40/MK801 conjugate on cumulative food intake in mice.

FIG. 9 shows the effect of GLP-1 Cys40/MK801 (100 nmol/kg) or equimolar doses of GLP-1 Cys40 or MK801 on cumulative food intake (FI Cumulative) in DIO mice treated for 10 days. Data is expressed as mean±SEM, N=8 per group. Over the course of the 10 days of treatment, a lowered cumulative food intake was observed in mice treated with GLP-1 Cys40 and GLP-1 Cys40/MK801 compared to the control (vehicle) and to MK801. Best results were observed for GLP-1 Cys40/MK801-treated mice which had a cumulative food intake of approximately 13 g/day, which is approximately 10 g/day less than the vehicle-treated mice (approximately 23 g/day).

Figure 10:
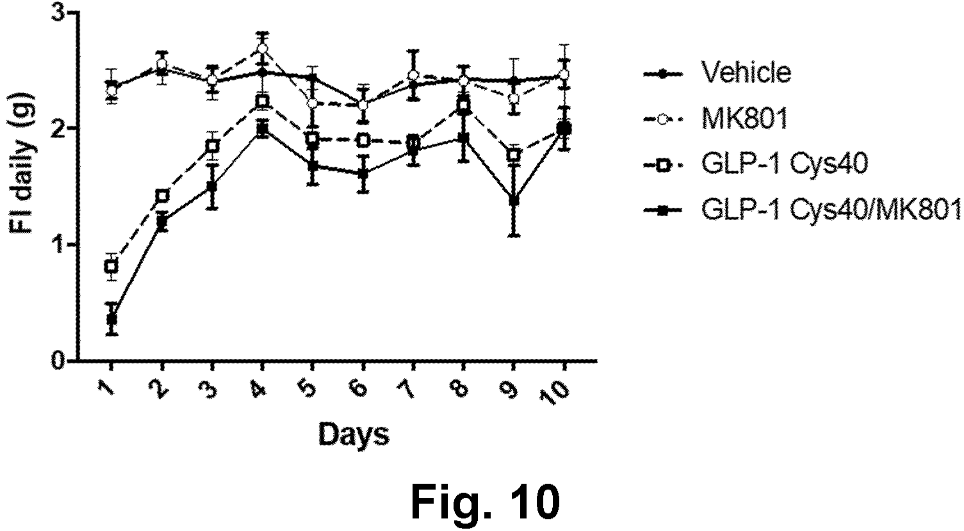
FIG. 10 shows the effect of GLP-1 Cys40/MK801 conjugate on daily food intake in mice.

FIG. 10 shows the effect of GLP-1 Cys40/MK801 (100 nmol/kg) or equimolar doses of GLP-1 Cys40 or MK801 on daily food intake (FI daily) in DIO mice treated for 10 days. Data is expressed as mean±SEM, N=8 per group. In general, the daily food intake fluctuated at varying degrees during the 10-days treatment, however, a reduction in food intake was observed all 10 days in mice treated with GLP-1 Cys40/MK801 compared to the control group (vehicle).

Figure 11:
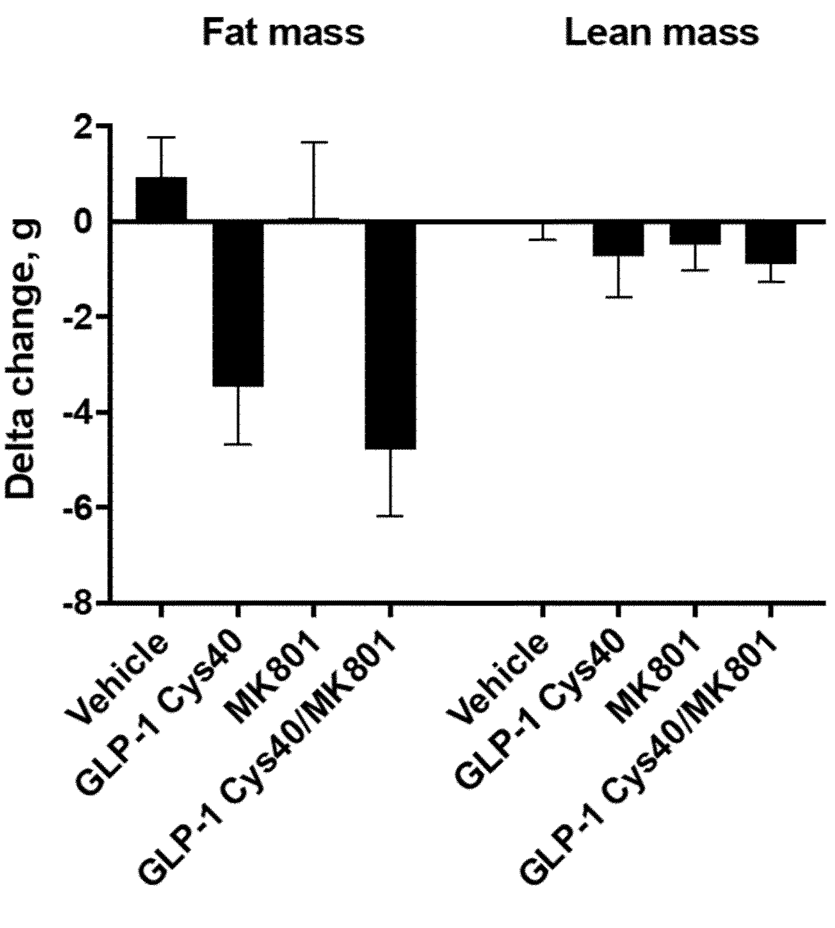
FIG. 11 shows the effect of GLP-1 Cys40/MK801 conjugate on body composition in mice.

FIG. 11 shows the effect of GLP-1 Cys40/MK801 (100 nmol/kg) or equimolar doses of GLP-1 Cys40 or MK801 on body composition (Delta change, g), in terms of change in fat and lean body mass, in DIO mice treated for 10 days. Data is expressed as mean±SEM and N=8 per group. After the 10-days treatment, the group of GLP-1 Cys40/MK801-treated mice displayed a reduction in both fat and lean body mass, with the change in fat mass (reduction of almost 5 g) being most prominent.

Figure 12:
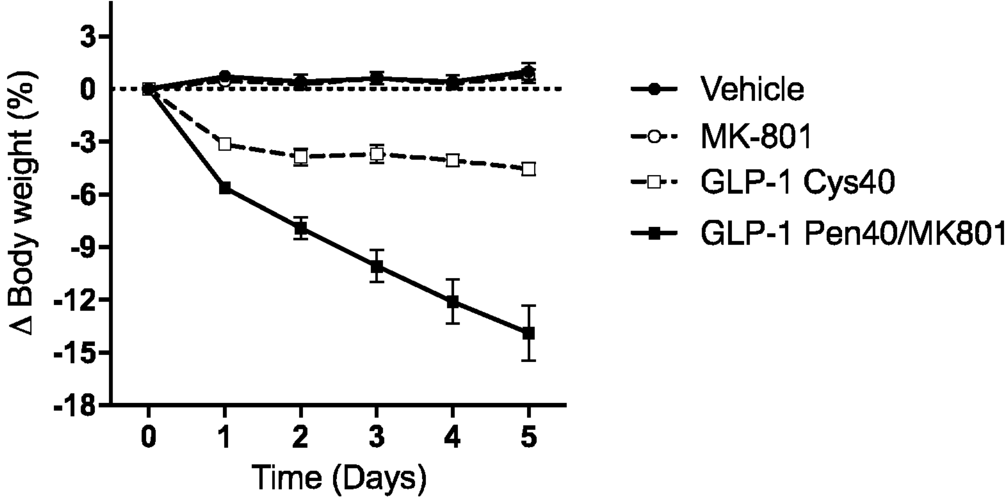
FIG. 12 shows the weight-lowering effect of a conjugate of a peptide of SEQ ID NO:1 and MK801 (GLP-1 Pen40/MK801), wherein the cysteine residue in SEQ ID NO:1 has been substituted by L-penicillamine.

FIG. 12 shows the effect of GLP-1 Pen40/MK801 (100 nmol/kg) or equimolar doses of GLP-1 Cys40 or MK801 on body weight % of DIO mice treated for 5 days. Data is expressed as mean±SEM, N=8 per group. After 5 days of treatment, GLP-1 Pen40/MK801-treated mice showed approximately 15% body weight reduction. In comparison GLP-1 Cys40-treated mice showed approximately 4% body weight reduction.

Figure 13:
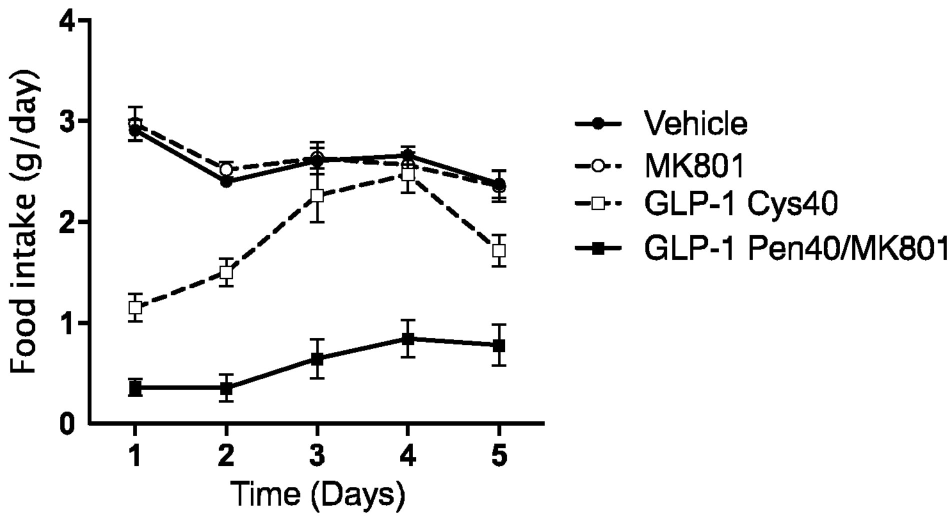
FIG. 13 shows the effect of GLP-1 Pen40/MK801 conjugate on daily food intake in mice.

FIG. 13 shows the effect of GLP-1 Pen40/MK801 (100 nmol/kg) or equimolar doses of GLP-1 Cys40 or MK801 on food intake (g/day) in DIO mice treated for 5 days. Data is expressed as mean±SEM, N=8 per group. Mice treated with GLP-1 Pen40/MK801 displayed an instant reduction in food intake compared to the control group (vehicle-treated mice). Furthermore, the lowered food intake was sustained at around 0.2-0.7 g/day during the 5-days treatment period.

Figure 14:
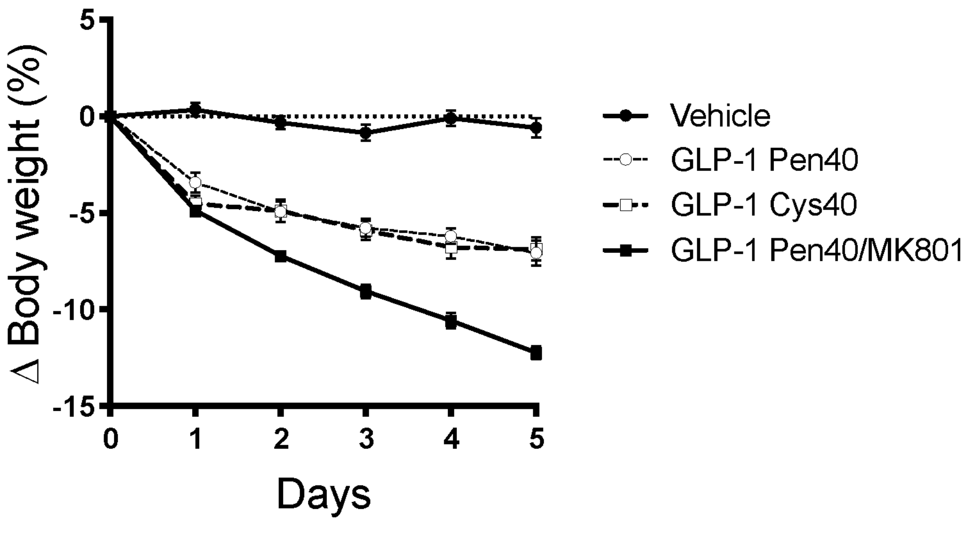
FIG. 14 shows the effect of GLP-1 Pen40/MK801 conjugate on body weight in mice.

FIG. 14 shows the effect of GLP-1 Pen40/MK801 (100 nmol/kg) or equimolar doses of GLP-1 Pen40 or GLP-1 Cys40 on body weight % in DIO mice treated for 5 days. Data is expressed as mean±SEM, N=7 per group. Mice treated with GLP-1 Pen40 or GLP-1 Cys40 displayed similar reductions in body weight % (approximately 6%), while the GLP-1 Pen40/MK801 showed approximately 12% reduction in body weight. Additionally, based on the slope of the curve, it would seem that a further reduction in body weight could be expected for the GLP-1 Pen40/MK801 if the treatment was extended.

Figure 21:
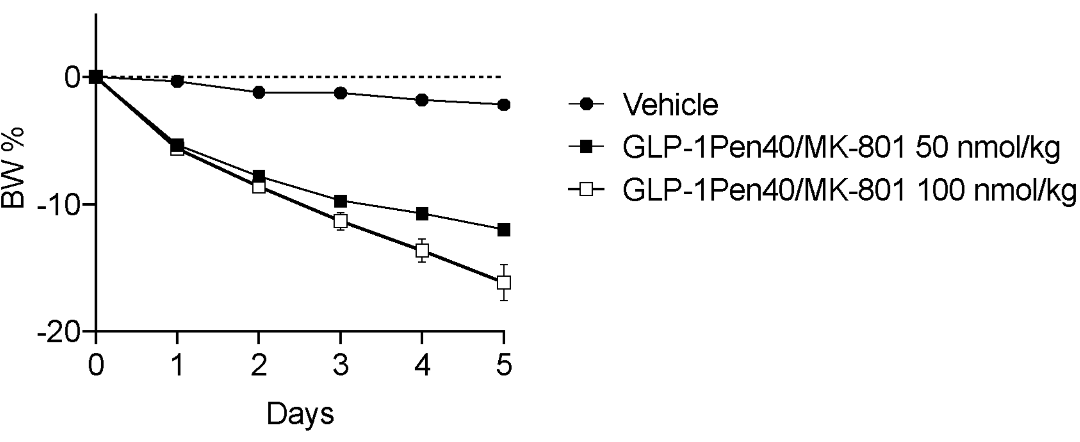
FIG. 21 shows the effect of different doses of GLP-1 Pen40/MK801 conjugate on body weight in mice.
Figure 22:
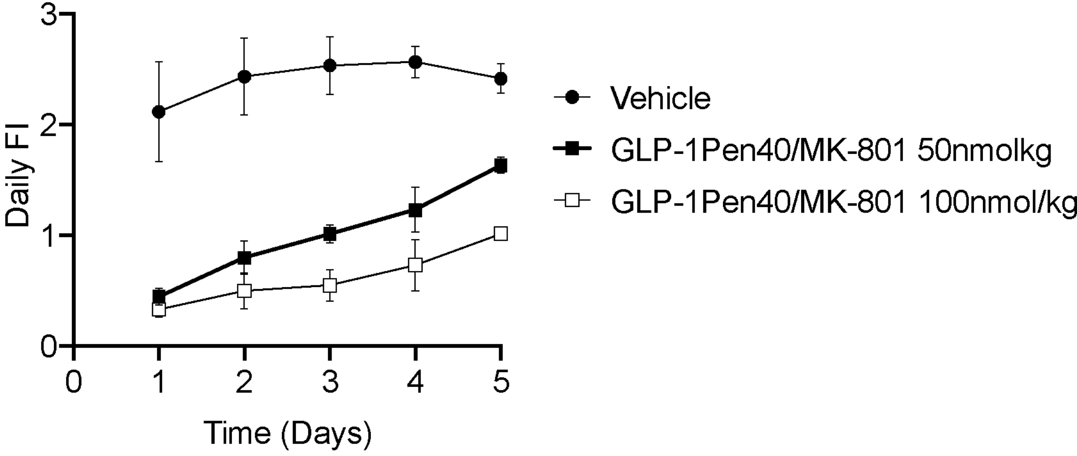
FIG. 22 shows the effect of different doses of GLP-1 Pen40/MK801 conjugate on daily food intake in mice.

FIGS. 21 and 22 show the effect of different doses (50 nmol/kg and 100 nmol/kg) of GLP-1 Pen40/MK801 conjugate compared to a control group (Vehicle, i.e. saline) on body weight (BW %, FIG. 21) and daily food intake (Daily FI in grams, FIG. 22) in DIO mice treated for 5 days. Data is expressed as mean±SEM, N=5 to 6 per group. Over the course of the treatment, a lowered body weight and daily food intake was observed for mice treated with both doses (50 nmol/kg and 100 nmol/kg) compared to the control group, with the most significant reduction observed for mice subjected to daily subcutaneous injections of 100 nmol/kg of the conjugate.

Figure 23:
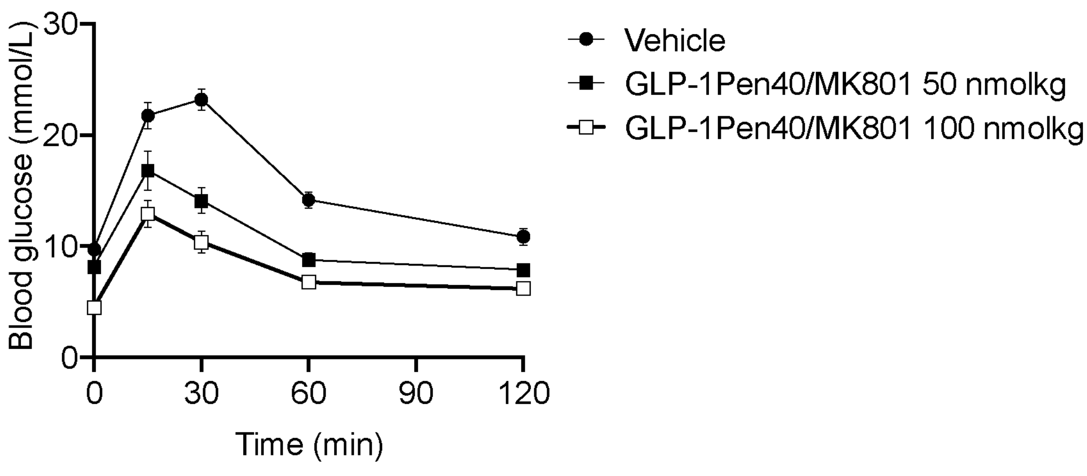
FIG. 23 shows the effect of different doses of GLP-1 Pen40/MK801 conjugate on blood glucose in mice after a compound tolerance test.

FIG. 23 shows the effect of different doses (50 nmol/kg and 100 nmol/kg) of GLP-1 Pen40/MK801 conjugate compared to a control group (vehicle, i.e. saline) on blood glucose level (mmol/L) in DIO mice subjected to ipGTT on day 7 of the treatment course. The blood glucose levels were measured over a course of 120 minutes. Data is expressed as mean±SEM, N=5 to 6 per group. In general, both doses, i.e. 50 nmol/kg and 100 nmol/kg, of the conjugate result in a significantly lower initial increase and overall lower blood glucose levels compared to the control group.

Figure 24:
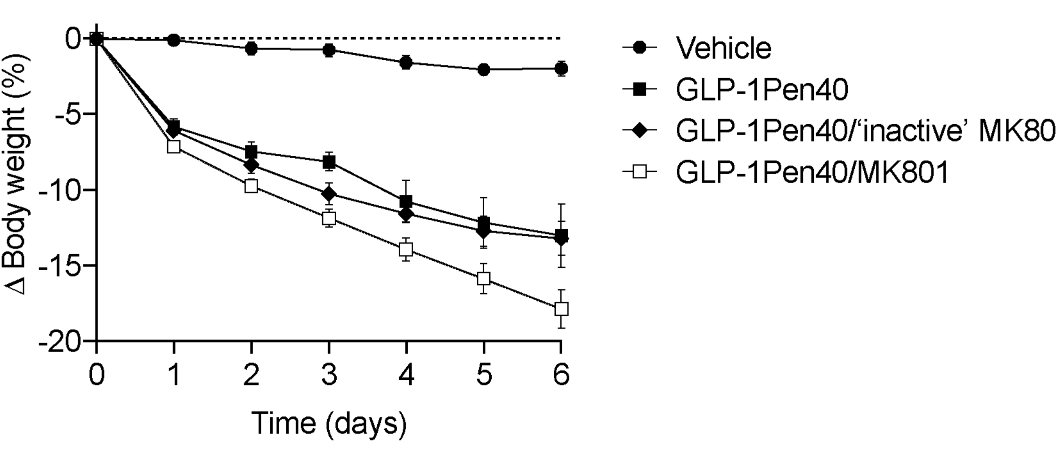
FIG. 24 shows the effect of active and inactive MK801 in a GLP-1 Pen40/MK801 conjugate on body weight in mice.
Figure 25:
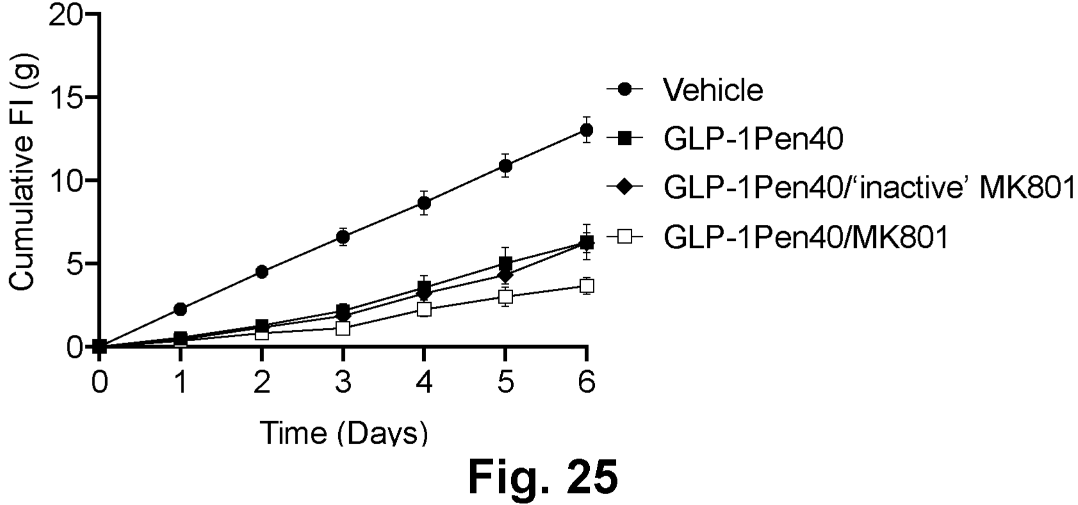
FIG. 25 shows the effect of active and inactive MK801 in a GLP-1 Pen40/MK801 conjugate on cumulative food intake in mice.

FIGS. 24 and 25 show the effect of active and inactive MK801 conjugated with GLP-1 Pen40 compared to a control group (vehicle, i.e. saline) on body weight (Δ Body weight in %, FIG. 24) and cumulative food intake (Cumulative FI in grams, FIG. 25) in DIO mice treated for 7 days. Data is expressed as mean±SEM, N=8 per group. Over the course of the treatment, a lowered body weight and cumulative food intake was observed for mice treated with GLP-1 Pen40 conjugated with active MK801. The conjugate with inactive MK801 showed similar results to unconjugated GLP-1 Pen40. It is concluded that MK801 and GLP-1 have a synergistic effect in reducing body weight and cumulative food intake in mice.

Figure 26:
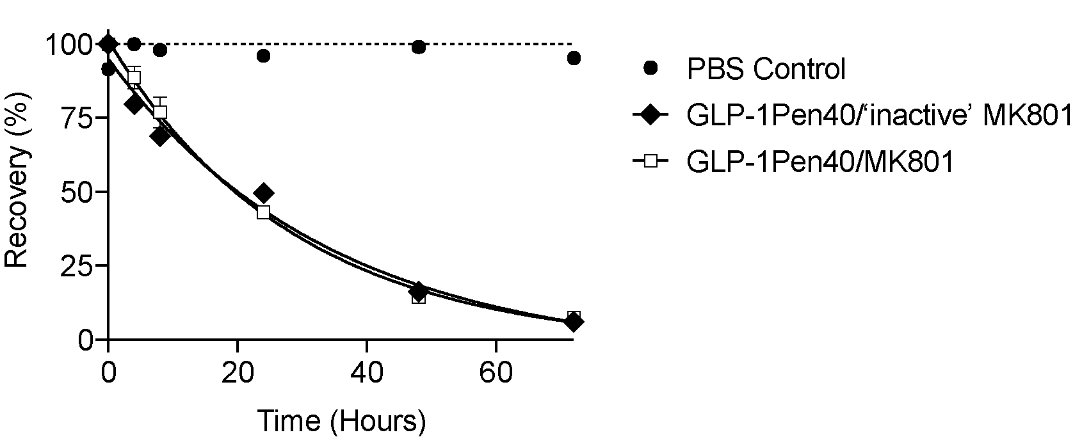
FIG. 26 shows the in vitro human plasma stability of active and inactive MK801 used for the conjugate GLP-1 Pen40/MK801.

FIG. 26 shows the in vitro human plasma stability of active and inactive MK801 versions of the conjugate GLP-1 Pen40/MK801 compared to a PBS control. The plasma stability of inactive and active MK801 is shown as percentage (%) recovery over time (hours). The two conjugates display nearly identical plasma stabilities independent of whether MK801 is active or inactive.

Figure 20:
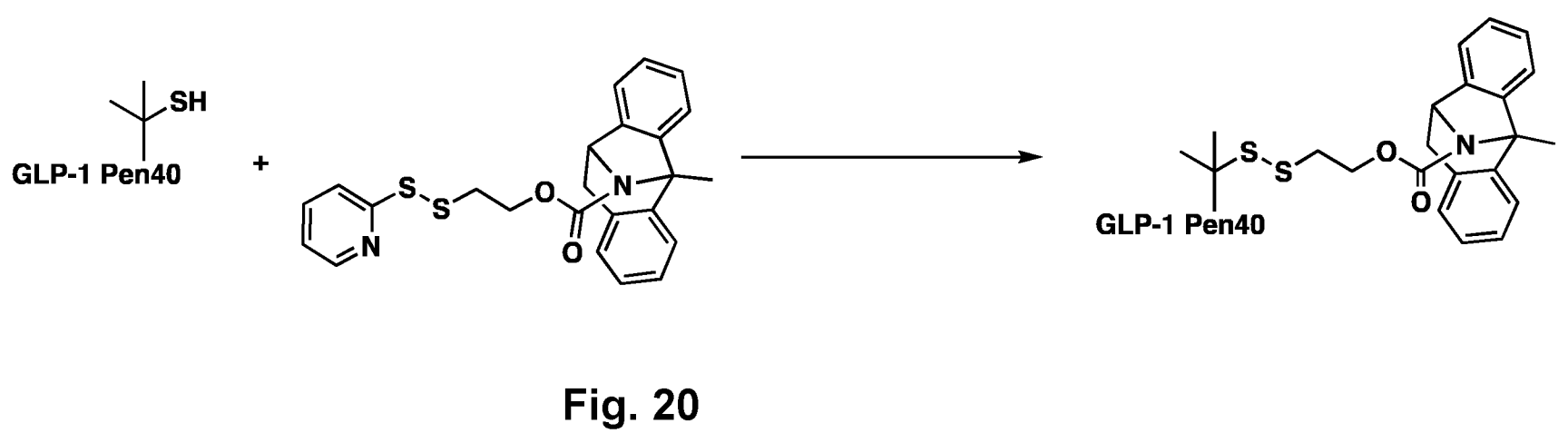
Figure 27:
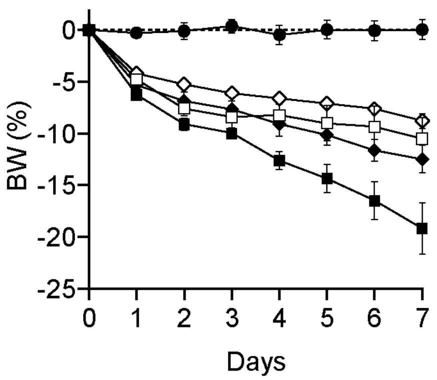
FIG. 27 shows the effect of GLP-1/MK801 conjugate with different linkers on body weight in mice.
Figure 28:
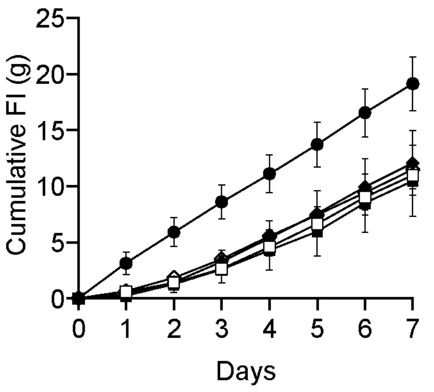
FIG. 28 shows the effect of GLP-1/MK801 conjugate with different linkers on cumulative food intake in mice.

FIGS. 27 and 28 show the effect of GLP-1/MK801 conjugate (100 nmol/kg) with different linkers compared to a control group (vehicle, i.e. saline) on body weight (BW in %, FIG. 27) and cumulative food intake (Cumulative FI in grams, FIG. 28) in DIO mice for 7 days. Data is expressed as mean±SEM, N=5 to 6 per group. The structures of the GLP-1/MK801 conjugates with different linkers are shown in FIG. 20 (GLP-1 Pen40/MK801), FIG. 29 (GLP-1 Lys40-triazole-$PEG_4$-Val-Cit-PAB-MK801)) and FIG. 30 (GLP-1 Cys40-mc-Val-Cit-PAB-MK801). Over the course of treatment, mice treated with conjugates of GLP-1/MK801 with different linkers showed similar reduction in cumulative food intake. The most significant reduction in body weight over the 7 days of treatment was observed for the group of mice treated with GLP-1 Pen40/MK801 conjugate (approximately 20% reduction).

Figure 31:
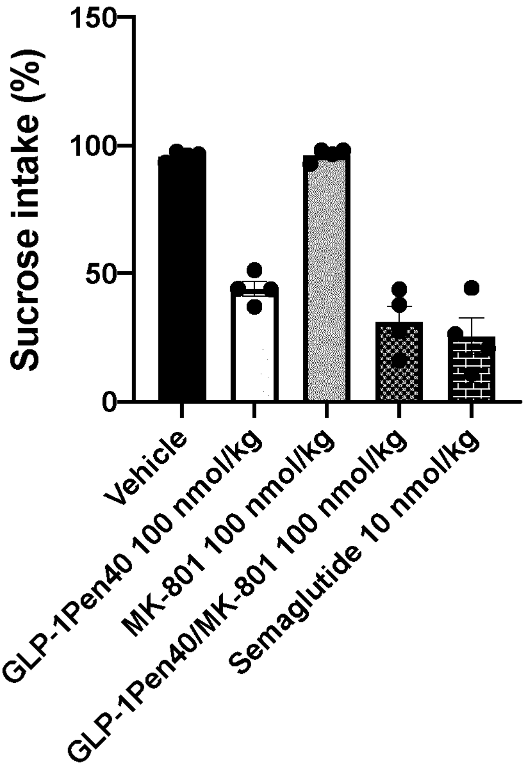
FIG. 31 shows the effect of GLP-1 Pen40/MK801 conjugate on sucrose intake in mice.

FIG. 31 shows the effect of GLP-1 Pen40/MK801 (100 nmol/kg) and equimolar doses of GLP-1 Pen40, MK801 or semaglutide on sucrose intake (in %) compared to the control group (vehicle, saline injection) in DIO mice treated for 8 days. Data is expressed as mean±SEM, N=8 per group. The most significant reduction in sucrose intake as expressed in comparison to the control group (vehicle) was observed for mice treated with semaglutide and the GLP-1/MK801 conjugate. It was concluded that the conjugated molecules of the invention are effective in inducing a food reward and satiety effect in the treated mice.

Figure 32:
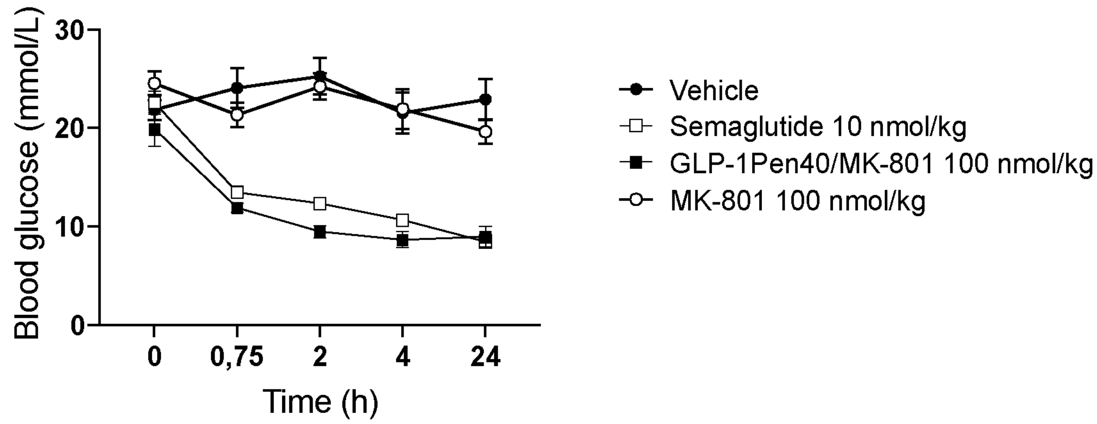
FIG. 32 show the effect of GLP-1 Pen40/MK801 conjugate on blood glucose in db/db mice after a compound tolerance test.

FIG. 32 shows the effect of GLP-1 Pen40/MK801 conjugate (100 nmol/kg) and equimolar doses of MK801 or semaglutide on blood glucose (mmol/L) in db/db (diabetic) mice subjected to ipGTT on day 7 of the treatment course. The blood glucose levels were measured over a course of 24 hours. Data is expressed as mean±SEM, N=8 per group. Mice treated with either semaglutide or the conjugate GLP-1 Pen40/MK801 displayed overall lower blood glucose levels compared to the control group (vehicle) and it was concluded that the conjugated molecule of the invention is suitable for treatment of diabetic mice.

FIGS. 33 and 34 show the effect of co-agonist GIP/GLP-1 Pen40/MK801 conjugate (SEQ ID NO:9) (50 nmol/kg) and a equimolar dose of GLP-1/GIP on body weight (in %, FIG. 33) and cumulative food intake (Cumulative FI in grams, FIG. 34) compared to the control group (vehicle, i.e. saline injection) in DIO mice treated for 7 days. Data is expressed as mean±SEM, N=8 per group. The most significant effect was observed in mice treated with the GIP/GLP-1/MK801 conjugate which mice showed an overall reduction in body weight of approximately 25% compared to the control group and an approximately 3 g cumulative food intake compared to the 15 g cumulative food intake observed for the control group.

FIGS. 36 to 38 show the effect of different NDMAR antagonists, i.e. MK801, memantine and neramexane, conjugated with GLP-1 Pen40 (100 nmol/kg) on body weight (in %, FIG. 36), daily food intake (Food intake, gram per day, FIG. 37), and cumulative food intake (cumulative FI in grams, FIG. 38) compared to the control group (vehicle, i.e. saline) in DIO mice treated for 5 days. Data is expressed as mean±SEM, N=8 per group. Over the course of the treatment, mice treated with the GLP-1 Pen40 conjugated with either MK801, memantine or neramexane all displayed a significant reduction in body weight and reduced daily and cumulative food intakes compared to the control group. It is concluded that different NMDAR antagonist may be conjugated to the peptides of the invention to obtain the same beneficial effect on body weight and food intake in mice.

Conclusion

The presented data demonstrate that chemical conjugation of a GLP-1 analogue and an NMDAR antagonist represents a novel medicinal strategy for effectively reversing obesity. Conjugates based on this strategy are superior in suppressing food intake and lowering body weight relative to the GLP-1 peptide control and are not flawed with adverse central effects of NMDAR antagonism.

EXAMPLES

Example 1: Preparation of Peptides and Peptide-NMDAR Antagonist Conjugates

Materials: All solvents and reagents were purchased from commercial sources and used without further purification. H-Rink amide ChemMatrix® resin was used for peptide elongation. Unless otherwise stated Fmoc-protected (9-fluorenylmethyl carbamate) amino acids were purchased from Iris-Biotech or Gyros Protein Technologies, and H-Rink amide ChemMatrix® resin, 35-100 mesh; loading of 0.40-

0.60 mmol/g from Sigma Aldrich. The commercially available $N^{\alpha}$-Fmoc amino acid building blocks were purchased as the following sidechain protected analogs: Arg, Pmc; Asp, $O^tBu$; Cys, Trt; Gln, Trt; His, Trt; Lys, Trt; Ser, $^tBu$; and Trp, Boc (Pmc=2,2,5,7,8-pentamethylchoman-6-sulfonyl, $O^tBu$=tert-butyl ester, Trt=trityl, Boc=tert-butyloxycarbonyl, and $^tBu$=tert-butyl ether).

All peptides and conjugates of peptides and NMDAR antagonists were characterized by analytical reverse phase ultra-performance liquid chromatography (RP-UPLC) (Waters) and electrospray ionization liquid chromatography mass spectrometry (ESI-LCMS) coupled to a Agilent 6410 Triple Quadrupole Massfilter with a C18 column (Zorbax Eclipse, XBD-C18, 4.6×50 mm). The ESI-LCMS was eluting with a binary buffer system composed of $H_2O$:MeCN:TFA (A: 95:5:0.1, B: 5:95:0.1) at a flow rate of 0.75 mL/min. Purities were determined by RP-UPLC equipped with a C18 column (Acquity UPLC BEH C18, 1.7 μm, 2.1×50 mm) eluting with a binary buffer system composed of $H_2O$:MeCN:TFA (A: 95:5:0.1, B: 5:95:0.1) at a flow rate of 0.45 mL/min.

Automated peptide synthesis protocol for Fmoc-protection scheme: Peptides were prepared as their C-terminally amidated derivatives using a Prelude X, induction heating assisted, peptide synthesizer (Gyros Protein Technologies, Tucson, AZ, USA) with 10 mL glass vessels. All reagents were freshly prepared as stock solutions in DMF: Fmoc-protected amino acid (0.2 M), HCTU (0.5 M), DIPEA (1.0 M) and piperidine (20% v/v). Peptide elongation was achieved by consecutive synthetic manipulations using the following protocol: Deprotection (2×2 min, RT, 300 rpm shaking) and coupling (2×5 min, 75° C., 300 rpm shaking, for Arg and His 2×5 min, 50° C., 300 rpm shaking). Peptides were prepared using double and triple couplings consisting of AA/HCTU/DIPEA (ratio 1:1.25:2.5) in 5-fold excess compared to the resin.

Peptide cleavage: The synthesised peptides were liberated from the peptidyl resin by addition of 1.5 mL cleavage cocktail (2.5% EDT, 2.5% $H_2O$, 2.5% TIPS, 2.5% thioanisole in TFA) per 100 mg peptidyl resin followed by agitation for 2 hours. The crude peptides were precipitated in cold diethyl ether, centrifuged at 2500×g for 10 min at 4° C., re-dissolved in MeCN:$H_2O$:TFA (ratio 1:1:0.01), filtered and lyophilized.

Purification: The crude peptide or conjugates of peptides and NMDAR antagonist was analyzed by RP-UPLC and ESI-LCMS or MALDI-TOF mass spectrometry prior to purification. Purifications were performed with a reverse-phase high-performance liquid chromatography (RP-HPLC) system (Waters) equipped with a reverse phase C18 column (Zorbax, 300 SB-C18, 21.2×250 mm) and eluting with a linear gradient (flow rate 20 mL/min) using a binary buffer system of $H_2O$:MeCN:TFA (A: 95:5:0.1; B: 5:95:0.1). Fractions were collected at intervals of 0.3 minutes and characterized ESI-LCMS. Purity was determined by RP-UPLC at 214 nm, and fractions with purities >95% were pooled and lyophilized. The final lyophilized products were used in further experiments.

Conjugation protocol for assembly of conjugates of peptides and NMDAR antagonists: The pure peptide and the pure thiopyridyl-activated NMDAR antagonist conjugate was dissolved in a binary solvent system (A: DMF; 6 M Guanidine, 1.5 M Imidazole in $H_2O$ at pH=8) (ratio 7:1) and agitated for at least 2 hours. The crude reaction mixture was monitored by analytical RP-UPLC and ESI-LCMS. Upon completion, the reaction mixture was diluted with buffer A and buffer B and purified directly using RP-HPLC eluting with a linear gradient.

Desalting: All peptides were desalted prior to biological experiments. Desalting was performed by consecutively re-dissolving the peptide or the conjugate of a peptide and an NMDAR antagonist in dilute aqueous 0.01 M HCl followed by lyophilization, repeated 3 times. The purity of the peptide or the conjugate was monitored by RP-UPLC and ESI-LCMS before being used for in vivo or in vitro experiments.

Preparation of GLP-1 Cys40/Memantine (Cysteine Linked).

A GLP-1 peptide with the amino acid sequence of SEQ ID NO:1 was synthesized using the Fmoc protocol as described above and conjugated to a chemical linker derivatized memantine analog. Synthesis of chemical linker derivatized memantine was performed via the synthetic route shown in FIG. 15. The first step in the synthetic route took place in MeOH at room temperature for 2 hours. The second step was carried out in $CH_2Cl_2$ in the presence of pyridine at 0° C. for 2 hours. The third step was carried out in DMF in the presence of N,N-Diisopropylethylamine (DIPEA) at 55° C. for 5 days. The final step (conjugation) was performed in a 6M guanidine, 1.5M imidazole buffer at room temperature for 2 hours.

2'-Pyridyldithio ethanol. In a dry round-bottomed flask equipped with a magnetic stirring bar and under $N_2$ atmosphere, 2'-aldrithiol (4.71 g, 21.3 mmol, 3 equiv.) was dissolved in dry MeOH (20 mL), followed by dropwise addition of 2-mercaptoethanol (0.56 g, 7.1 mmol, 0.5 mL, 1 equiv.) via a syringe. The reaction was left for 2 hours at ambient temperature before concentrated in vacuo. The crude yellow oil was purified by silica gel flash chromatography (EtOAc:$CH_2Cl_2$, 2:8), affording 2'-Pyridyldithio ethanol as a clear oil (1.33 g, 100%). $R_f$=0.48; $^1$H NMR (600 MHz, Chloroform-d) δ 8.49 (d, J=5.0 Hz, 1H), 7.57 (td, J=7.7, 1.8 Hz, 1H), 7.44-7.36 (m, 1H), 7.16-7.11 (m, 1H), 5.32 (s, 1H), 3.88-3.73 (m, 2H), 3.01-2.89 (m, 2H); $^{13}$C NMR (151 MHz, $CDCl_3$) δ 159.31, 149.86, 137.00, 122.12, 121.57, 58.37, 42.83.

4-nitrophenyl (2-(pyridin-2-yldisulfaneyl)ethyl) carbonate. To a dry round-bottomed flask equipped with a magnetic stirring bar and under $N_2$-atmosphere, 2'-Pyridyldithio ethanol (1.33 g, 7.1 mmol, 1 equiv.) and dry pyridine (0.56 g, 8.5 mmol, 0.575 mL, 1.2 equiv.) was diluted in anhydrous $CH_2Cl_2$ (15 mL). The reaction mixture was cooled to 0° C. and nitrophenyl chloroformate (1.72 g, 8.5 mmol, 1.2 equiv.) was added in one portion. The reaction was stirred for 10 minutes, allowed to reach ambient temperature and left for 2 hours under stirring. The reaction was diluted to 50 mL and extracted with 3× $H_2O$ (30 mL) and brine (30 mL), dried over $MgSO_4$, filtered and concentrated in vacuo. The crude oil was purified by silica gel flash chromatography (Heptanes:EtOAc, 2:1), affording 4-nitrophenyl (2-(pyridin-2-yldisulfaneyl)ethyl) carbonate as a clear viscous oil (2.21 g, 89%). $R_f$=0.34; Purity >95% (HPLC), $R_t$=15.99 min; UPLC/MS (ESI): m/z calcd. for $C_{14}H_{12}N_2O_5S_2$ $[M+H]^+$=353.0, found 353.3 m/z; $^1$H NMR (600 MHz, DMSO-$d_6$) δ 8.47 (ddd, J=4.8, 1.9, 0.9 Hz, 1H), 8.35-8.26 (m, 2H), 7.84 (td, J=7.8, 1.8 Hz, 1H), 7.78 (dt, J=8.1, 1.1 Hz, 1H), 7.58-7.48 (m, 2H), 7.26 (ddd, J=7.3, 4.8, 1.1 Hz, 1H), 4.48 (t, J=6.0 Hz, 2H), 3.24 (t, J=6.1 Hz, 2H); $^{13}$C NMR (151 MHz, DMSO) δ 158.65, 155.17, 151.75, 149.66, 145.18, 137.80, 125.40, 122.53, 121.40, 119.52, 66.54, 36.42.

2-(pyridin-2-yldisulfaneyl)ethyl (3,5-dimethyladamantan-1-yl)carbamate In a dry round-bottomed flask equipped with a magnetic stirring bar and under $N_2$, 4-nitrophenyl (2-(pyridin-2-yldisulfaneyl)ethyl) carbonate (707 mg, 2.00 mmol, 1 equiv.) and Memantine hydrochloride (650 mg, 3.00 mmol, 1.5 equiv.) were dissolved in dry DMF (20 mL) and dry DIPEA (260 mg, 6.00 mmol, 0.35 mL, 3 equiv.) was added via syringe. Memantine was not completely dissolved and upon addition of DIPEA, the reaction turned yellow immediately. The reaction was left for 5 days followed by heating to 80° C. The reaction was then transferred to a separatory funnel with EtOAc (50 mL) and washed exhaustively with 5× half. Sat brine (50 mL) and brine (50 mL) to remove DMF. The organic layer was subsequently extracted 5×1 M aqueous NaOH (50 mL) (Until the yellow color of the aqueous layer ceased), dried over $MgSO_4$, filtered and concentrated in vacuo. The crude oil was purified by silica gel flash chromatography eluting with a gradient (Heptanes: EtOAc, 9:1 to 3:1), affording 2-(pyridin-2-yldisulfaneyl) ethyl (3,5-dimethyladamantan-1-yl)carbamate as a glassy viscous oil (540 mg, 54%). $R_f$=0.26; Purity >95% (HPLC), $R_t$=19.36 min; UPLC/MS (ESI): m/z calcd. for $C_{20}H_{28}N_2O_2S_2$ $[M+H]^+$=393.2, found 393.4 m/z; $^1$H NMR (600 MHz, DMSO-$d_6$) δ 8.46 (ddd, J=4.8, 1.9, 0.9 Hz, 1H), 7.85-7.75 (m, 2H), 7.25 (ddd, J=7.2, 4.8, 1.2 Hz, 1H), 6.89 (s, 1H), 4.10 (t, J=6.4 Hz, 2H), 3.05 (t, J=6.3 Hz, 2H), 1.69-1.63 (m, 2H), 1.54-1.43 (m, 4H), 1.31-1.20 (m, 5H), 1.07 (s, 2H), 0.80 (s, 6H); $^{13}$C NMR (151 MHz, DMSO) δ 159.04, 153.78, 149.55, 137.79, 121.21, 119.23, 60.80, 51.40, 50.18, 47.07, 42.22, 37.46, 31.84, 30.05, 29.46.

GLP-1 Cys40 and GLP-1 Cys40/Memantine was prepared using the protocols described above. RP-UPLC and ESI-LCMS analyses determined the purity to >95%.

Preparation of GLP-1 Pen40/Memantine (Penicillamine Linked).

Figure 15:
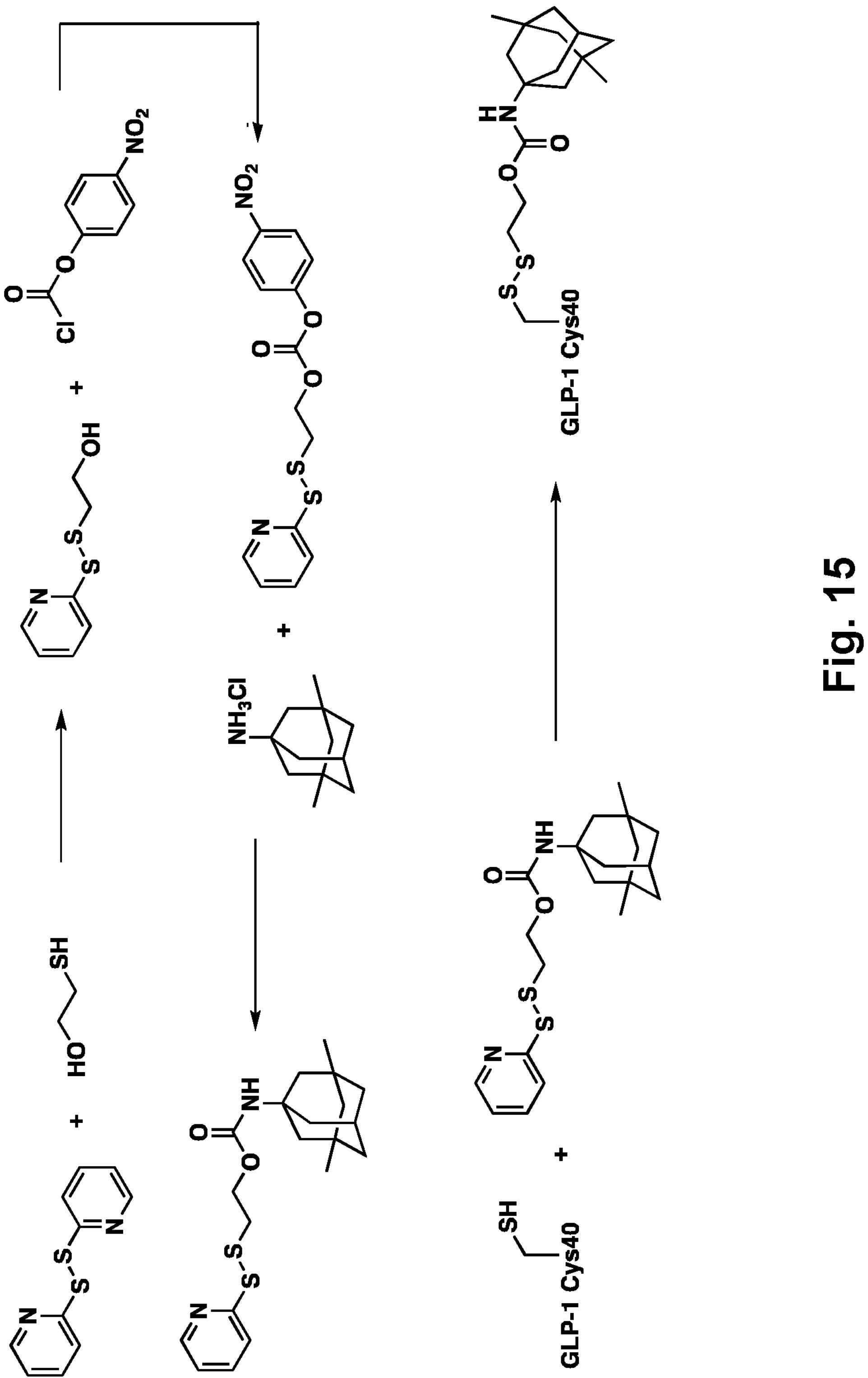
FIG. 15 shows a synthesis route of a chemical linker derivatized memantine.
Figures 16, 17:
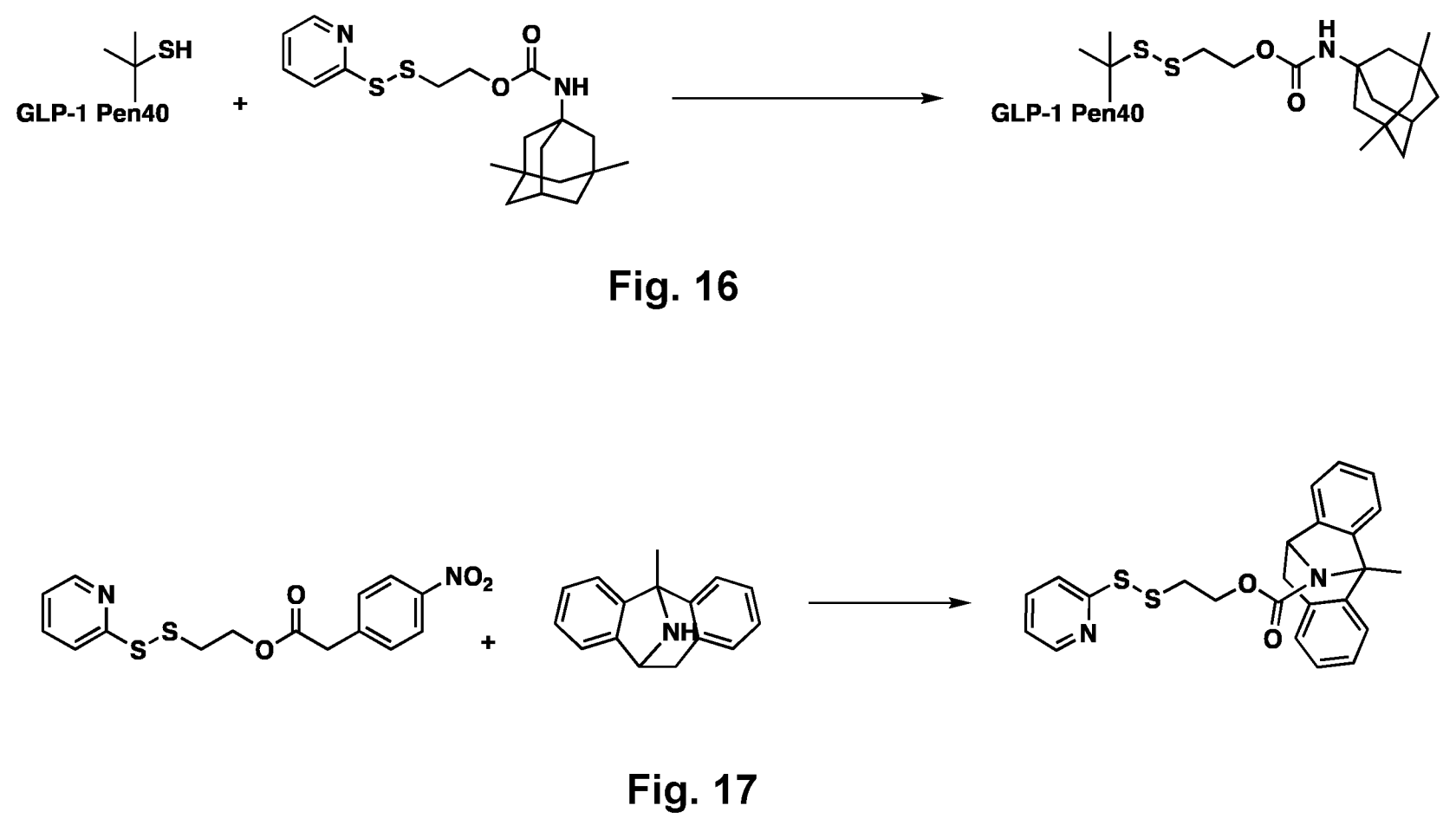

Synthesis of chemical linker derivatized memantine was performed using the synthetic route disclosed in FIG. 15. GLP-1 Pen40 and memantine were conjugated by the chemical reaction shown in FIG. 16, which was carried out in 6M guanidine, 1.5M imidazole buffer at room temperature for 2 hours.

Preparation of GLP-1 Cys40/MK801 (Cysteine Linked).

A peptide with the sequence of SEQ ID NO:1 was synthesized using the Fmoc protocol disclosed above and conjugated with a chemical linker derivatized MK801 analog. Synthesis of chemical linker derivatized MK801 was performed via the second synthetic route disclosed in FIG. 17. The chemical reaction was performed in DMF in the presence of DIPEA at 55° C. for 5 days.

Figures 18, 19:
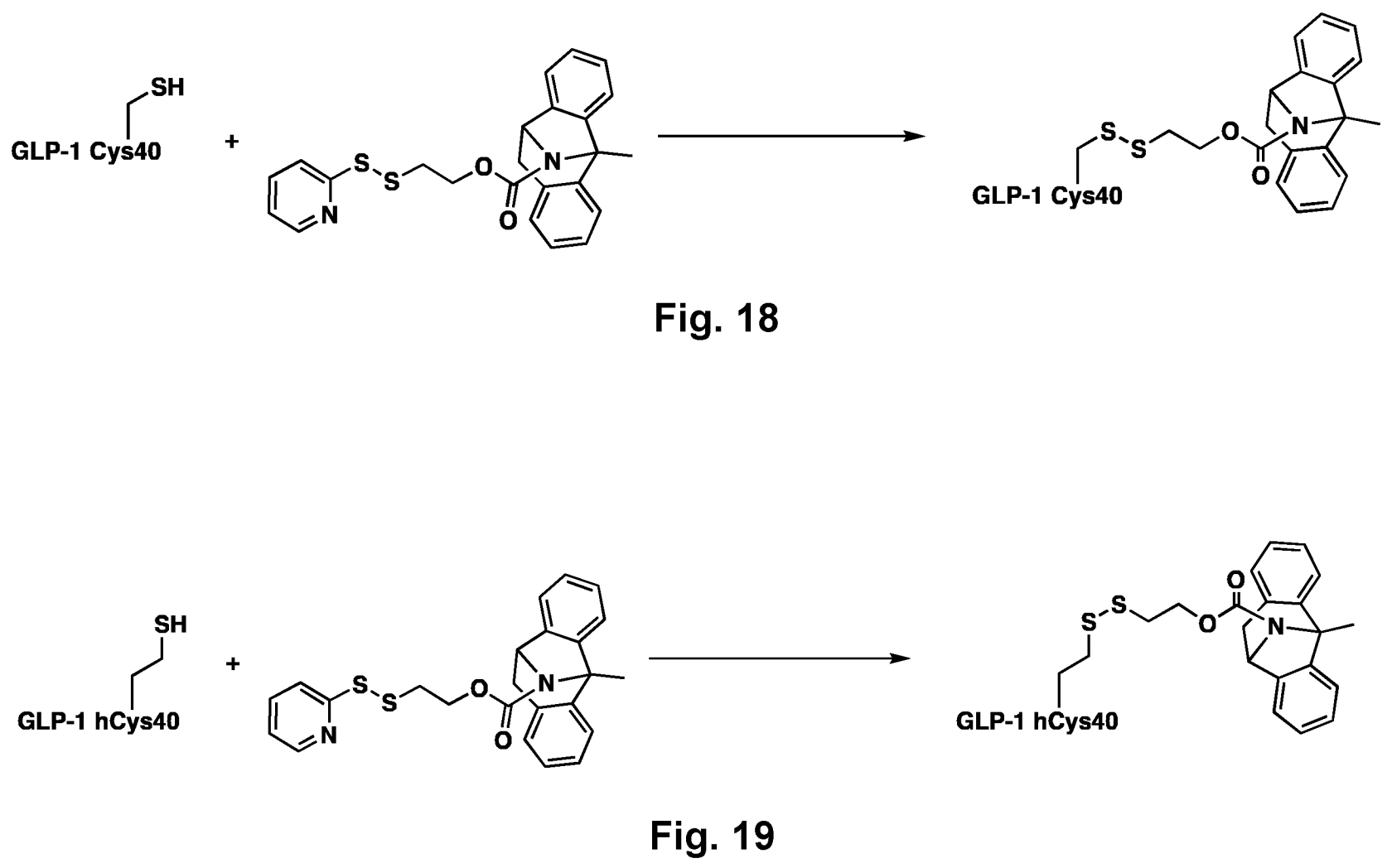

Linker derivatized MK801 was conjugated to GLP-1 Cys40 by the chemical reaction shown in FIG. 18. The reaction was performed in a 6M guanidine, 1.5M imidazole buffer at room temperature for 2 hours.

2-(pyridin-3-yldisulfaneyl)ethyl 5-methyl-10,11-dihydro-5H-5,10-epiminodibenzo[a,d][7]annulen e-12-carboxylate. In a flame-dried schlenk round-bottomed flask equipped with a magnetic stirring bar and under $N_2$ atmosphere, MK801 hydrochloride 191 mg, 0.86 mmol, 1.2 equiv.) was dissolved in dry DMF (10 mL) followed by addition of 4-nitrophenyl (2-(pyridin-2-yldisulfaneyl)ethyl) carbonate (253 mg, 0.72 mmol, 1.0 equiv.). Subsequently, dry DIPEA (375 μL, 2.14 mmol, 3.0 equiv.) was added and the solution turned yellow. The reaction was heated to 55° C. in an oil-bath and stirred for 4 days—until UPLC-MS indicated full consumption of the starting material. The reaction was diluted with EtOAc (50 mL) and washed thoroughly with half sat. brine (5×60 mL), 0.5 M aq. NaOH (5×60 mL) and brine. The organic layer was collected, dried over $MgSO_4$, filtered and concentrated in vacuo. Purification by preparative HPLC (eluting with isocratic 60% B, over 17 mL/min) followed by lyophilization afforded 11 as a clear solid (250.2 mg, 80.1%); Purity >95% (HPLC), $R_t$=18.17 min; UPLC/MS (ESI): m/z calcd. for $C_{24}H_{22}N_2O_2S_2$ $[M+H]^+$=435.1, found 435.4; $^1$H NMR (600 MHz, DMSO-$d_6$) δ 8.41 (dt, J=4.8, 1.4 Hz, 1H), 7.68 (dt, J=7.9, 4.1 Hz, 2H), 7.45 (d, J=7.1 Hz, 1H), 7.38-7.31 (m, 1H), 7.25-7.15 (m, 4H), 7.15-7.06 (m, 2H), 7.01-6.87 (m, 1H), 5.38 (d, J=5.5 Hz, 1H), 4.27-4.13 (m, 2H), 3.59 (dd, J=17.3, 5.7 Hz, 1H), 3.10 (s, 2H), 2.67-2.58 (m, 1H), 2.20 (s, 3H); $^{13}$C NMR (151 MHz, DMSO) δ 158.92, 149.56, 143.37, 139.04, 137.70, 131.78, 130.25, 127.42, 127.34, 127.31, 125.88, 122.12, 121.66, 121.20, 119.19, 65.33, 62.21, 59.20, 37.55.

GLP-1 Cys40/MK801 was prepared from 2-(pyridin-3-yldisulfaneyl)ethyl 5-methyl-10,11-dihydro-5H-5,10-epiminodibenzo[a,d][7]annulen e-12-carboxylate and GLP-1 Cys40 using the protocol disclosed above. RP-UPLC and ESI-LCMS analyses confirmed the product and determined the purity to >95%.

Preparation of GLP-1 hCys40/MK801 (Homocysteine Linked).

A peptide with the amino acid sequence of SEQ ID NO:1 and the hCys40 modification was synthesized using the Fmoc protocol disclosed above and conjugated with a chemical linker derivatized MK801 analog. The chemical synthesis of linker derivatized MK801 was performed via the synthetic route shown in FIG. 19, the chemical reaction being performed in 6M guanidine, 1.5M imidazole buffer at room temperature for 2 hours.

GLP-1 hCys40: A peptide with the amino acid sequence of SEQ ID NO:1 and the hCys40 modification was prepared using the protocol disclosed above. RP-UPLC and ESI-LCMS analyses determined the purity to >95%. GLP-1 hCys40/MK801 was prepared using the protocol disclosed above. RP-UPLC and ESI-LCMS analyses determined the purity to >95%.

Preparation of GLP-1 Pen40/MK801 (Penicillamine Linked).

A GLP-1 peptide derivative was synthesized using the Fmoc protocol disclosed above and conjugated with a chemical linker derivatized MK801 analog. The chemical synthesis of the chemical linker derivatized MK801 was performed via the route disclosed in FIG. 16.

GLP-1 Pen40/MK801: The conjugate was prepared using the protocol disclosed above and by the chemical reaction shown in FIG. 20, the chemical reaction being performed in 6M guanidine, 1.5M imidazole buffer at room temperature for 2 hours. RP-UPLC and ESI-LCMS analyses determined the purity to >95%.

Example 2: Investigation of In Vitro Human Plasma Stability

In vitro human plasma stability assay: Peptide stabilities were determined using normal human plasma containing citrate phosphate dextrose (3H Biomedical, lot P22). The human plasma was pre-heated at 37° C. for 15 min. Subsequently, 360 μL human plasma was spiked with 40 μL of GLP-1 Pen40/MK801, GLP-1 hCys40/MK801, or GLP-1 Cys40/MK801 conjugate stock solution (1 mM, prepared by dilution with PBS buffer from a 10 mM peptide in DMSO stock) and incubated under light shaking at 37° C. Aliquots of 45 μL were collected at t=0 and 5 additional timepoints (depending on the stability of the conjugate) and pre-treated with urea buffer (50 μL, 30 min) at 0° C., following treatment with 20% trichloroacetic acid in acetone and incubation at −20° C. overnight. After centrifugation (13400 rpm, 30 min), the supernatant was filtered and analyzed by RP-UPLC at 214 nm and ESI-LCMS. The area under the curve (AUC) was determined and plotted using prism 8.0. The half-lives ($T_{1/2}$) were determined by fitting the data to a one-phase decay equation. The data is represented as the mean of three individual experiments.

Example 3: In Vivo Pharmacology Studies in Diet-Induced Obesity (DIO) Mice

C57BL6J male mice, in the following referred to as diet-induced obesity (DIO) mice, were maintained on a high-fat diet (58% energy from fat) and had, for each study, an average body weight of more than 45 gram prior to study start. Mice were either housed individually or double-housed. The mice were maintained on a 12 h dark-light cycle at 21-23° C. Compounds were administered subcutaneously once daily (between 2 pm-5 pm) and food intake (FI) and body weight (BW) measured at the corresponding time. For body composition, measures of fat and lean mass were performed prior to the study (1-3 days prior to study start) and on the final day of the study using an MRI scanner (EchoMRI). The group of mice injected with a vehicle (saline) served as the control group.

Example 4: Sucrose Preference Test in Chow-Fed Mice

C57BL6J male mice were single housed in cages and maintained on a chow diet. Compounds were administered subcutaneously once daily at a dose of 100 nmol/kg for all compounds, except semaglutide which was administered at a dose of 10 nmol/kg. The group of mice injected with a vehicle (saline) served as the control group. 8 mice were included in each treatment group. All cages were equipped with two drinking bottles and the mice acclimatized for a minimum of five days prior to start of the study. Upon study start, the water bottles were replaced by one bottle containing water and one bottle containing an aqueous sucrose solution of 10% (w/v). The sucrose bottles were distributed equally as the left and right bottle to correct for side preferences. Sucrose water intake and water intake were measured after 24 hours by weighing the bottles.

The invention claimed is:

1. A conjugated molecule comprising a peptide and an N-methyl-D-aspartate receptor (NMDAR) antagonist selected from the group consisting of MK801, neramexane, memantine, memantine hydrochloride, amantadine, ketamine, phencyclidine (PCP), and norketamin, wherein the peptide is covalently bonded to the NMDAR antagonist either directly or through a chemical linker, and wherein the peptide comprises at least 80% amino acid sequence identity to the amino acid sequence of SEQ ID NO: 1 or 9.

2. The conjugated molecule according to claim 1, wherein the NMDAR antagonist in its free form has a dissociation constant $K_d$ with an NMDA receptor in the range of about 0.5 nM to 1000 nM.

3. The conjugated molecule according to claim 1, wherein the peptide has at least 80% amino acid sequence identity to SEQ ID NO:1.

4. The conjugated molecule according to claim 1, wherein the NMDAR antagonist is covalently bonded at the C-terminal region of the peptide.

5. The conjugated molecule according to claim 1, wherein the NMDAR antagonist is covalently bonded to the peptide via a cleavable chemical linker; wherein the cleavable chemical linker is selected from the group consisting of acid-cleavable linkers, enzyme-cleavable linkers, peptide-cleavable linkers, and linkers comprising a disulfide group.

6. The conjugated molecule according to claim 5, wherein the chemical linker has the formula $R_1$-$R_3$—S—S—$R_4$-$R_5$—O—CO—$R_2$; wherein $R_1$ is the peptide; $R_2$ the NMDAR antagonist; $R_3$ is optional and when present is selected from $C(CH_3)_2$, $CH_2$—$CH_2$, or $CH_2$, bonded to a side chain of the peptide or to a carbon atom of the backbone chain of the peptide; $R_4$ is $(CH_2)_n$ or $C_6H_4$; and $R_5$ is optional and when present is selected from $C(CH_3)_2$, $CH_2$—$CH_2$, or $CH_2$, and n is 1, 2, 3 or 4.

7. The conjugated molecule according to claim 1, wherein the NMDAR antagonist is covalently bonded via an —SH of a cysteine, a homocysteine or an L penicillamine at the C-terminal of the peptide.

8. The conjugated molecule according to claim 1, wherein the peptide displays at least 30% activity of native glucagon-like peptide 1 (GLP-1) at the GLP-1 receptor.

9. The conjugated molecule according to claim 1, wherein the peptide has at least 90% amino acid sequence identity to the amino acid sequence of SEQ ID NO: 1 or 9.

10. A pharmaceutical composition comprising the conjugated molecule according to claim 1 or a pharmaceutically acceptable salt thereof and a pharmaceutically acceptable carrier.

11. A method of treatment of obesity, binge eating disorder, insulin resistance, type 2 diabetes, dyslipidaemia, non-alcoholic steatohepatitis, or non-alcoholic fatty liver disease, comprising administering the conjugated molecule according to claim 1 to a subject in need thereof.

12. A method of reducing body weight of a mammal comprising administering the conjugated molecule according to claim 1 to the mammal in need thereof.

13. A non-therapeutic method of treatment of a mammal for reducing body weight, which method comprises orally administering to said mammal in need thereof the conjugated molecule according to claim 1.

14. The non-therapeutic method of treatment of a mammal for reducing body weight according to claim 13, wherein the mammal has a non-pathogenic body mass index (BMI).

* * * * *

SEQUENCE LISTING

```
<160> NUMBER OF SEQ ID NOS: 9

<210> SEQ ID NO 1
<211> LENGTH: 40
<212> TYPE: PRT
<213> ORGANISM: Homo sapiens
<220> FEATURE:
<223> OTHER INFORMATION: GLP-1 modified
<220> FEATURE:
<221> NAME/KEY: VARIANT
<222> LOCATION: 2
<223> OTHER INFORMATION: D-alanine, D-serine, alpha-aminoisobutyric
      acid, N-methyl-serine, glycine, or valine
<220> FEATURE:
<221> NAME/KEY: VARIANT
<222> LOCATION: 40
<223> OTHER INFORMATION: L-penicillamine or L-homocysteine

<400> SEQUENCE: 1

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro Ser
            20                  25                  30

Ser Gly Ala Pro Pro Pro Ser Cys
        35                  40


<210> SEQ ID NO 2
<211> LENGTH: 108
<212> TYPE: PRT
<213> ORGANISM: Homo sapiens
<220> FEATURE:
<223> OTHER INFORMATION: Growth Hormone Releasing Hormone
      (Somatoliberin)

<400> SEQUENCE: 2

Met Pro Leu Trp Val Phe Phe Phe Val Ile Leu Thr Leu Ser Asn Ser
1               5                   10                  15

Ser His Cys Ser Pro Pro Pro Pro Leu Thr Leu Arg Met Arg Arg Tyr
            20                  25                  30

Ala Asp Ala Ile Phe Thr Asn Ser Tyr Arg Lys Val Leu Gly Gln Leu
        35                  40                  45

Ser Ala Arg Lys Leu Leu Gln Asp Ile Met Ser Arg Gln Gln Gly Glu
    50                  55                  60
```

```
Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95

Ala Leu Leu Gln Lys His Ser Arg Asn Ser Gln Gly
            100                 105


<210> SEQ ID NO 3
<211> LENGTH: 170
<212> TYPE: PRT
<213> ORGANISM: Homo sapiens
<220> FEATURE:
<223> OTHER INFORMATION: Vasoactive Intestinal Peptide

<400> SEQUENCE: 3

Met Asp Thr Arg Asn Lys Ala Gln Leu Leu Val Leu Leu Thr Leu Leu
1               5                   10                  15

Ser Val Leu Phe Ser Gln Thr Ser Ala Trp Pro Leu Tyr Arg Ala Pro
            20                  25                  30

Ser Ala Leu Arg Leu Gly Asp Arg Ile Pro Phe Glu Gly Ala Asn Glu
        35                  40                  45

Pro Asp Gln Val Ser Leu Lys Glu Asp Ile Asp Met Leu Gln Asn Ala
    50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110

Ser Asn Ile Ser Glu Asp Pro Val Pro Val Lys Arg His Ser Asp Ala
        115                 120                 125

Val Phe Thr Asp Asn Tyr Thr Arg Leu Arg Lys Gln Met Ala Val Lys
    130                 135                 140

Lys Tyr Leu Asn Ser Ile Leu Asn Gly Lys Arg Ser Ser Glu Gly Glu
145                 150                 155                 160

Ser Pro Asp Phe Pro Glu Glu Leu Glu Lys
                165                 170


<210> SEQ ID NO 4
<211> LENGTH: 27
<212> TYPE: PRT
<213> ORGANISM: Homo sapiens
<220> FEATURE:
<223> OTHER INFORMATION: Pituitary Adenylate Cyclase-Activating
      Polypeptide 27

<400> SEQUENCE: 4

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25


<210> SEQ ID NO 5
<211> LENGTH: 121
<212> TYPE: PRT
<213> ORGANISM: Homo sapiens
<220> FEATURE:
<223> OTHER INFORMATION: Secretin

<400> SEQUENCE: 5
```

```
Met Ala Pro Arg Pro Leu Leu Leu Leu Leu Leu Leu Leu Gly Gly Ser
1               5                   10                  15

Ala Ala Arg Pro Ala Pro Pro Arg Ala Arg Arg His Ser Asp Gly Thr
            20                  25                  30

Phe Thr Ser Glu Leu Ser Arg Leu Arg Glu Gly Ala Arg Leu Gln Arg
        35                  40                  45

Leu Leu Gln Gly Leu Val Gly Lys Arg Ser Glu Gln Asp Ala Glu Asn
    50                  55                  60

Ser Met Ala Trp Thr Arg Leu Ser Ala Gly Leu Leu Cys Pro Ser Gly
65                  70                  75                  80

Ser Asn Met Pro Ile Leu Gln Ala Trp Met Pro Leu Asp Gly Thr Trp
                85                  90                  95

Ser Pro Trp Leu Pro Pro Gly Pro Met Val Ser Glu Pro Ala Gly Ala
            100                 105                 110

Ala Ala Glu Gly Thr Leu Arg Pro Arg
        115                 120


<210> SEQ ID NO 6
<211> LENGTH: 42
<212> TYPE: PRT
<213> ORGANISM: Homo sapiens
<220> FEATURE:
<223> OTHER INFORMATION: Gastric inhibitory polypeptide

<400> SEQUENCE: 6

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40


<210> SEQ ID NO 7
<211> LENGTH: 31
<212> TYPE: PRT
<213> ORGANISM: Homo sapiens
<220> FEATURE:
<223> OTHER INFORMATION: Exendin-4

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 8
<211> LENGTH: 39
<212> TYPE: PRT
<213> ORGANISM: Homo sapiens
<220> FEATURE:
<223> OTHER INFORMATION: GLP-1 unmodified

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

-continued

```
<210> SEQ ID NO 9
<211> LENGTH: 40
<212> TYPE: PRT
<213> ORGANISM: Homo sapiens
<220> FEATURE:
<223> OTHER INFORMATION: GLP-1/GIP co-agonist
<220> FEATURE:
<221> NAME/KEY: VARIANT
<222> LOCATION: 2
<223> OTHER INFORMATION: D-alanine, D-serine, alpha-aminoisobutyric
      acid, N-methyl-serine, glycine, or valine
<220> FEATURE:
<221> NAME/KEY: VARIANT
<222> LOCATION: 20
<223> OTHER INFORMATION: D-alanine, D-serine, alpha-aminoisobutyric
      acid, N-methyl-serine, glycine, or valine
<220> FEATURE:
<221> NAME/KEY: VARIANT
<222> LOCATION: 40
<223> OTHER INFORMATION: L-penicillamine or L-homocysteine

<400> SEQUENCE: 9

Tyr Gly Glu Gly Thr Phe Thr Ser Asp Tyr Ser Ile Tyr Leu Asp Lys
1               5                   10                  15

Gln Ala Ala Lys Glu Phe Val Asn Trp Leu Leu Ala Gly Gly Pro Ser
            20                  25                  30

Ser Gly Ala Pro Pro Pro Ser Cys
        35                  40
```